(12) United States Patent
Bakos et al.

(10) Patent No.: US 10,376,265 B2
(45) Date of Patent: Aug. 13, 2019

(54) NON-MAGNETIC FRAGMENTABLE TISSUE COMPRESSION DEVICES

(71) Applicant: ETHICON LLC, Guaynabo, PR (US)

(72) Inventors: Gregory J. Bakos, Mason, OH (US); Daniel J. Mumaw, Liberty Township, OH (US); Brian F. DiNardo, Cincinnati, OH (US); Frederick E. Shelton, IV, Hillsboro, OH (US); Robert P. Kruth, Fort Wayne, IN (US)

(73) Assignee: Ethicon LLC, Guaynabo, PR (US)

( * ) Notice: Subject to any disclaimer, the term of this patent is extended or adjusted under 35 U.S.C. 154(b) by 20 days.

(21) Appl. No.: 15/419,426

(22) Filed: Jan. 30, 2017

(65) Prior Publication Data

US 2018/0214154 A1 Aug. 2, 2018

(51) Int. Cl.
*A61B 17/11* (2006.01)
*A61B 17/064* (2006.01)
*A61B 17/00* (2006.01)

(52) U.S. Cl.
CPC ...... *A61B 17/1114* (2013.01); *A61B 17/0643* (2013.01); *A61B 2017/00004* (2013.01);
(Continued)

(58) Field of Classification Search
CPC ................. A61B 17/11; A61B 17/1114; A61B 2017/00004; A61B 2017/00876;
(Continued)

(56) References Cited

U.S. PATENT DOCUMENTS

| 5,346,501 A | * | 9/1994 | Regula ................ A61B 17/1114 |
| | | | 606/151 |
| 6,171,320 B1 | | 1/2001 | Monassevitch |
| | | | (Continued) |

FOREIGN PATENT DOCUMENTS

WO WO 2012/007042 A1 1/2012

OTHER PUBLICATIONS

Ryou, M. et al, "Endoscopic Intestinal Bypass Creation by Using Self-Assembling Magnets in a Porcine Model." Gastrointestinal Endoscopy, vol. 83, No. 4, pp. 821-825, 2016 (abstract only).
(Continued)

*Primary Examiner* — Diane D Yabut
(74) *Attorney, Agent, or Firm* — Frost Brown Todd LLC

(57) ABSTRACT

Devices are used to modify a metabolic pathway of a digestive system by creating a pathway within the intestinal tract through an anastomosis between a proximal location within the intestinal tract and a distal location within the intestinal tract. An anastomosis compression assembly includes a first portion and a second portion, each including two or more segments securely fixed together by a pair of degradable joining members, and each further including interlocking mechanisms. The first portion and second portion are configured to be coupled together from different locations within the intestinal tract by the application of force. Once aligned, the first and second portions are securely attached to one another by engaging their respective interlocking mechanisms. After completion of the anastomosis procedure, the degradable links degrade and separate the anastomosis compression assembly into smaller fragments for ease of passage through the patient's intestinal tract.

20 Claims, 18 Drawing Sheets

(52) U.S. Cl.
CPC ............... *A61B 2017/00876* (2013.01); *A61B 2017/1117* (2013.01); *A61B 2017/1132* (2013.01); *A61B 2017/1139* (2013.01)

(58) Field of Classification Search
CPC ..... A61B 2017/1117; A61B 2017/1132; A61B 2017/1103
See application file for complete search history.

(56) References Cited

U.S. PATENT DOCUMENTS

| | | | |
|---|---|---|---|
| 7,445,622 B2 | 11/2008 | Ortiz et al. | |
| 7,637,919 B2 | 12/2009 | Ishikawa et al. | |
| 7,674,271 B2 | 3/2010 | Bjerken | |
| 7,780,686 B2 | 8/2010 | Park et al. | |
| 8,142,454 B2 | 3/2012 | Harrison et al. | |
| 8,197,498 B2 | 6/2012 | Coleman et al. | |
| 8,684,995 B2 | 4/2014 | Sato et al. | |
| 8,828,031 B2 | 9/2014 | Fox et al. | |
| 8,828,032 B2 | 9/2014 | McWeeney et al. | |
| 8,864,781 B2 | 10/2014 | Surti et al. | |
| 8,870,899 B2 | 10/2014 | Beisel et al. | |
| 9,282,993 B1* | 3/2016 | Cohen | A61B 17/3421 |
| 9,364,238 B2 | 6/2016 | Bakos et al. | |
| 9,381,041 B2 | 7/2016 | Brown et al. | |
| 9,456,820 B2 | 10/2016 | Gagner et al. | |
| 2003/0144675 A1* | 7/2003 | Nicolo | A61B 17/0643 606/153 |
| 2005/0209614 A1 | 9/2005 | Fenter et al. | |
| 2006/0036267 A1 | 2/2006 | Saadat et al. | |
| 2007/0142850 A1 | 6/2007 | Fowler | |
| 2011/0137394 A1 | 6/2011 | Lunsford et al. | |

OTHER PUBLICATIONS

Ryou, M. et al, "Minimally Invasive Entero-Enteral Dual-Path Bypass Using Self-Assembling Magnets." Surgical Endoscopy, Springer, Feb. 19, 2016 (abstract only).
U.S. Appl. No. 15/298,816, filed Oct. 20, 2016.
U.S. Appl. No. 61/697,845, filed Sep. 7, 2012.
International Search Report and Written Opinion dated Apr. 9, 2018 for Application No. PCT/IB2018/050356, 13 ps.

* cited by examiner

NON-MAGNETIC FRAGMENTABLE TISSUE COMPRESSION DEVICES

BACKGROUND

In some instances, it may be desirable to provide a side-to-side anastomosis between two naturally occurring lumens within a patient's body. By way of example only, it may be desirable to provide an anastomosis between two portions of a patient's gastrointestinal tract, such as between the patient's duodenum and the patient's ileum. In some patients, it may improve glucose control, serve as a treatment for type 2 diabetes, and/or provide other results when the jejunum is diverted by an anastomosis. In such a procedure, a first enterotomy may be formed in the sidewall of the duodenum while a second enterotomy is formed in the sidewall of the ileum. The sidewalls may then be positioned adjacent to each other to form an anastomosis between the portions of the duodenum and the ileum in which the enterotomies are formed, as described in greater detail below. The anastomosis establishes direct fluid communication between the adjacent portions of the duodenum and ileum, enabling at least some nutrient-rich chyme to pass through the anastomosis to travel from the duodenum directly to the ileum without passing through the jejunum. In other variations in which the anastomosis is positioned at other locations within the gastrointestinal tract, some chyme may pass through a shortened portion of the jejunum. In either case, the anastomosis enables accelerated passage of nutrient-rich chyme through the gastrointestinal tract.

One or more devices may be positioned within the first and second enterotomies to hold the sidewalls of the duodenum and ileum together, thereby holding the first and second openings in alignment with each other and maintaining patency through the openings. The device or devices may compress the tissue, which may ultimately result in a serosa-to-serosa adhesion that secures the duodenum sidewall to the ileum sidewall. In addition, tissue captured in the device or devices may eventually necrose, such that the device or devices is/are eventually released into the gastrointestinal tract and subsequently passed through the bowels. Traditional examples of anastomosis devices include Denan's rings and the Murphy button. Examples of anastomosis procedures and associated devices are taught in U.S. Provisional Patent App. No. 61/697,845, entitled "Magnetic Compression Anastomosis Device," filed Sep. 7, 2012, the disclosure of which is incorporated by reference herein; U.S. Pat. No. 9,364,238, entitled "Method and Apparatus for Joining Hollow Organ Sections in Anastomosis," issued Jun. 14, 2016, the disclosure of which is incorporated by reference herein; and U.S. patent application Ser. No. 15/298,816, entitled "Method for Partial Diversion of the Intestinal Tract," filed Oct. 20, 2016, published as U.S. Pub. No. 2017/0035425 on Feb. 9, 2017, the disclosure of which is incorporated by reference herein.

While a variety of anastomosis devices and methods have been made and used, it is believed that no one prior to the inventor(s) has made or used an invention as described herein.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

Figure 1:
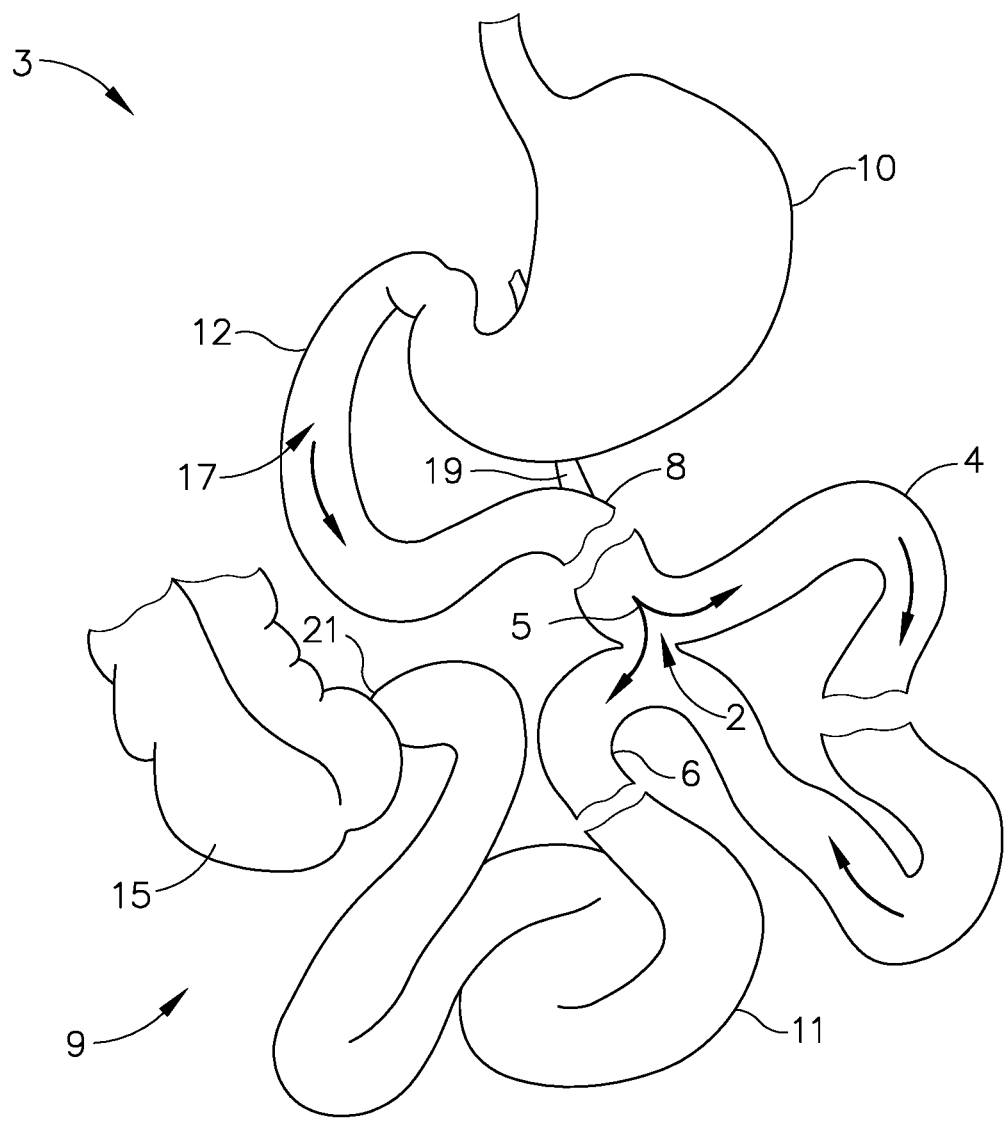
FIG. 1 depicts a diagrammatic view of a portion of a patient's digestive system, showing an anastomosis in the small intestines to divert chyme from the patient's jejunum.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. EXEMPLARY INTESTINAL ANASTOMOSIS

As noted above, it may be desirable to provide an anastomosis between two naturally occurring lumens within a patient's body, such as within the patient's gastrointestinal tract. FIG. 1 shows an example of an anastomosis (2) formed between a proximal portion of a patient's jejunum (4) and the patient's ileum (6). The anastomosis (2) is located just distal to the duodenojujenal flexure (8). The anastomosis (2) provides a path for fluid communication from the proximal portion of a patient's jejunum (4) directly to the ileum (6), thereby providing a bypass of the majority of the jejunum (4). In particular, chyme that exits the stomach (10) may flow directly through the duodenum (12), then through just the proximal portion of the jejunum (4) and directly to the ileum (6) via the anastomosis (2), without passing through the majority of the jejunum (4). In some instances, a portion of the chyme that exits the stomach (10) flows directly from the proximal portion of the jejunum (4) to the ileum (6) via the anastomosis (2); while another portion passes the anastomosis (2) and flows through the remainder of the jejunum (4). Thus, anastomosis (2) may form a complete diversion of chyme or a partial diversion of chyme.

It should be understood that it may be necessary to create at least two enterotomies in order to provide an anastomosis (2)—one opening for the upstream region of the lumen and another opening for the downstream region of the lumen. The tissue surrounding the two enterotomies may be secured together with the enterotomies in alignment in order to provide the anastomosis (2). Once these openings are aligned at the site of the anastomosis (2), a device may be used to compress and hold the tissue together to maintain alignment of the enterotomies forming the anastomosis (2). Holding the tissue together may promote serosa-to-serosa adhesion, such that the serosa that is apposed at the anastomosis (2) eventually bonds together and thereby maintains structural integrity of the anastomosis (2) without the need for assistance by a surgically introduced device. In some instances, it may be necessary to create one or more additional enterotomies in the gastrointestinal tract in order to surgically introduce a device that compresses the tissue together to maintain alignment of the openings forming the anastomosis (2). These additional enterotomies may need to be closed (e.g., using suture, etc.) after the anastomosis compression device has been introduced to the site of the anastomosis (2). The creation and subsequent closure of these additional access enterotomies may impose additional time, cost, and/or risk in the surgical procedure.

The following disclosure includes examples of anastomosis compression devices that may be used to compress and hold the tissue together to maintain alignment and patency of the openings forming the anastomosis (2). It should be understood that each of these devices may be introduced into the lumens of the jejunum and ileum via the same enterotomies that will eventually form the anastomosis (2). In other words, it is not necessary to create (and subsequently close) any additional enterotomies in order to position the below described devices at the site of the anastomosis (2). It should also be understood that the devices described below are configured to maintain their positions at the anastomosis (2) without requiring the devices to be sutured in place. The devices include one device portion that is placed in one part of the gastrointestinal tract and another device portion that is placed in another part of the gastrointestinal tract. These device portions are biased toward each other (e.g., by a resilient member, by magnetic forces, etc.) and thereby compress tissue between opposing surfaces of the device portions. The compression provides a fluid-tight seal at the anastomosis (2), preventing chyme, etc. from leaking at the anastomosis (2). The edges of the opposing device surfaces that contact tissue are rounded or chamfered to prevent the device portions from cutting through the tissue of the gastrointestinal tract. The compressed tissue eventually necroses due to ischemia, such that the device portions and necrosed tissue eventually leave the anastomosis (2) and pass through the gastrointestinal tract.

Figure 2:
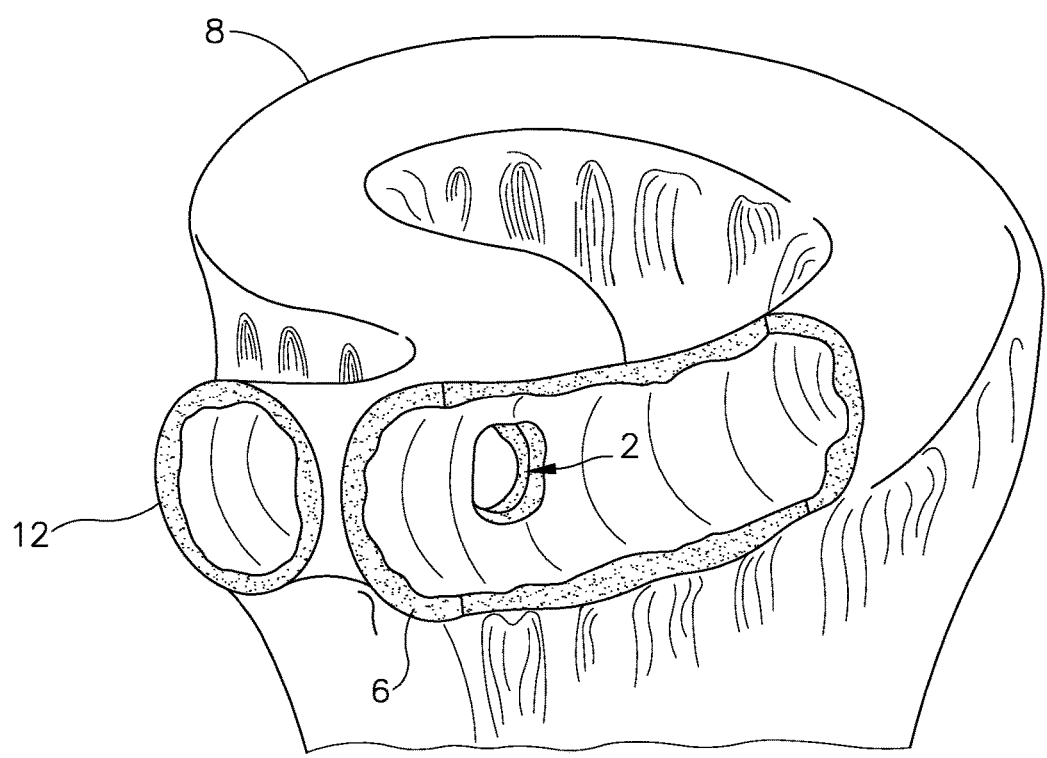
FIG. 2 depicts a partial perspective view of another exemplary anastomosis to divert chyme from the patient's jejunum.

While FIG. 1 shows the anastomosis (2) positioned just distal to the duodenojujenal flexure (8) (e.g., approximately 100 cm distal to the duodenojujenal flexure (8)) and coupling the proximal portion of the jejunum (4) with the ileum (6), it should be understood that an anastomosis (2) may be positioned at various other suitable locations within the gastrointestinal tract. For instance, an anastomosis (2) may be located proximal to the duodenojujenal flexure (8), thus directly coupling the duodenum (12) with the ileum (6) such that chyme may bypass the entire length of the jejunum (4) as shown in FIG. 2. In another example, an anastomosis (2) may be located about 100 centimeters distal to the duodenojujenal flexure (8) and/or ligament of Treitz (19). As another merely illustrative example, an anastomosis (2) may provide a direct coupling between the stomach (10) and jejunum (4), such that chyme may bypass the duodenum (12); or between the esophagus and stomach (10) to re-connect the tract after removing a portion of the esophagus; or between the colon and rectum after removing a portion of the colon due to a lesion, etc. In some examples, the anastomosis (2) may have a side-to-side orientation to connect adjacent portions of a lumen such as the small intestine. Other suitable locations for an anastomosis (2) within the gastrointestinal tract will be apparent to those of ordinary skill in the art in view of the teachings herein. It should also be understood that an anastomosis (2) may be located elsewhere in a patient's body; and that an anastomosis need not necessarily be located within the patient's gastrointestinal tract. It is contemplated that the exemplary anastomosis compression devices described below (and variations thereof) may be used in various locations throughout a patient's body, not just the gastrointestinal tract. By way of example only, the devices described below (and variations thereof) may be used in a treatment for prolapsed hemorrhoids where the compression elements necrose and remove a portion of tissue without forming an anastomosis between hollow organs.

By way of further example, and not limitation, in one example a metabolic pathway of the digestive system (3) is modified by creating a pathway (5) within the intestinal tract (9) by establishing a connection between a proximal location within the small intestine (11) and a distal location within the intestinal tract (9). In the present example, the connection is formed by way of an anastomosis (2). In some examples, the connection is formed by way of a side-to-side anastomosis. Also in the present example, the proximal location within the small intestine (11) is distal to the duodenal papilla (17). In this manner, the pathway (5) serves as a shortcut added to the existing pathway defined by the intestinal tract (9) of the digestive system (3), such that the existing pathway of the intestinal tract (9) remains intact. Accordingly, the procedures involved to create the pathway (5) do not transect, remove, or seal off any portion of the digestive system (3). Furthermore, the procedure is thus fully reversible and the entire digestive system (3) can be fully returned to its original state.

In modifying the metabolic pathway of the digestive system (3) to create the pathway (5), the small intestine (11) itself defines a first initial length. The pathway (5) created defines a second length. This second length is represented as the bypassed region or bypass portion of the intestinal tract (9) that is created due to the anastomosis (2). In this manner, the bypassed region is that length of the intestinal tract (9) that chyme passing through the intestinal tract (9) would not travel through when the chyme instead follows the shortcut pathway created by the anastomosis (2). In this way, the second length can also be defined as the length commencing at the anastomosis (2) at the proximal location in the intestinal tract (9) and terminating at the anastomosis (2) at the distal location in the intestinal tract (9). In the present example the second length can be between about 10% and 70% of the first initial length of the small intestine (11). In one instance of the present example, the second length is less than about 60% of the initial overall length of the small intestine (11).

When performing the method to create the pathway (5) within the intestinal tract (9), natural orifice translumenal endoscopic surgery (also referred to as NOTES) may be used, where the procedure involves one or more flexible endoscopes that are inserted into a patient via a natural orifice of the patient. Such natural orifices can include the mouth or oral cavity for transgastric procedures, the anus for transcolonic procedures, and/or the vagina for transvaginal procedures. Such natural orifices are not limited to only those mentioned above, but may instead include any natural orifice of a patient. In some instances a previous scar site may be used to insert the one or more flexible endoscopes, such as through the navel or umbilicus. In view of the teachings herein, one skilled in the art will recognize that methods for enteroscopy such as double balloon enteroscopy or spiral enteroscopy using a system like the Endo-Ease Discovery® SB made by Spirus Medical, LLC can facilitate the identification of both proximal and distal locations via flexible endoscopy. Furthermore, some procedures for creating the pathway (5) may be performed completely endoscopically, completely laparoscopically, in a completely open procedure, or in a mix of any of these procedure types and/or in combination with natural orifice procedure types. In view of the teachings herein, the various types of procedures and levels of invasiveness that may be used with the methods of creating pathways within the intestinal tract (9) described herein will be apparent to those of ordinary skill in the art.

In the present example, the proximal location, in addition to being distal to the duodenal papilla (17), can be in the duodenum (12), jejunum (4), or the ileum (6). The distal location can be in the jejunum (4), ileum (6), or colon (15). In one instance of the present example, the proximal location is in the duodenum (12), while the distal location is in the jejunum (4). In another instance, the proximal location is in the duodenum (12), while the distal location is in the ileum (6). In another instance, the proximal location is in the jejunum (4), while the distal location is also in the jejunum (4). In another instance, the proximal location is in the jejunum (4), while the distal location is in the ileum (6). In another instance, the proximal location is in the jejunum (4), while the distal location is in the colon (15). In another instance, the proximal location is in the ileum (6), while the distal location is also in the ileum. In another instance, the proximal location is in the ileum (6), while the distal location is in the colon (15). In view of the teachings herein, other locations for the proximal location and the distal location for the created pathway (5) will be apparent to those of ordinary skill in the art.

In the example where the proximal location for the connection is in the jejunum (4) and the distal location is in the colon (15), in one instance the proximal location is at least about 200 centimeters distal from the ligament of Treitz (19). In the example where the proximal location for the connection is in the jejunum (4), in one instance, the proximal location is between about 10 centimeters and about 200 centimeters distal to the ligament of Treitz (19), and in another instance 100 centimeters distal to the ligament of Treitz (19). As mentioned above, in procedures where the proximal location for the connection is in the jejunum (4), one or more flexible endoscopes may be inserted into a patient via the oral cavity and/or the colon (15).

In the example where the distal location for the connection is in the ileum (6), in one instance the distal location is between about 10 centimeters and 300 centimeters proximal to the ileocecal junction (21), and in another instance 250 centimeters proximal to the ileocecal junction (21). In the example where the distal location for the connection is in the colon (15), it may be in either the ascending portion of the colon, the transverse portion of the colon, or the descending portion of the colon. In another example, the distal location is about 250 centimeters proximal to the ileocecal junction (21), while the proximal location is about 100 centimeters from the ligament of Treitz (19).

In an example where the connection is a side-to-side anastomosis (2), the procedure includes forming the anastomosis (2) by compression through an exemplary anastomosis compression assembly (100). In such procedures, a first portion (110) is introduced to a first attachment region at the proximal location and a second portion (130) is introduced to a second attachment region at the distal location. Also, the first portion (110) includes a surface that mates with, or is configured to be oriented adjacent to, a corresponding surface on the second portion (130). The procedure further includes compressing a first lumen wall at the first attachment region and a second lumen wall at the second attachment region between the first portion (110) and second portion (130) of the exemplary anastomosis compression assembly (100). Further exemplary features and functionalities that may be incorporated into anastomosis compression assembly (100) will be described in greater detail below; while others will be apparent to those of ordinary skill in the art in view of the teachings herein. It should be understood, however, that the anastomosis compression devices need not necessarily be used in all versions of the procedures described herein.

Figure 8A:
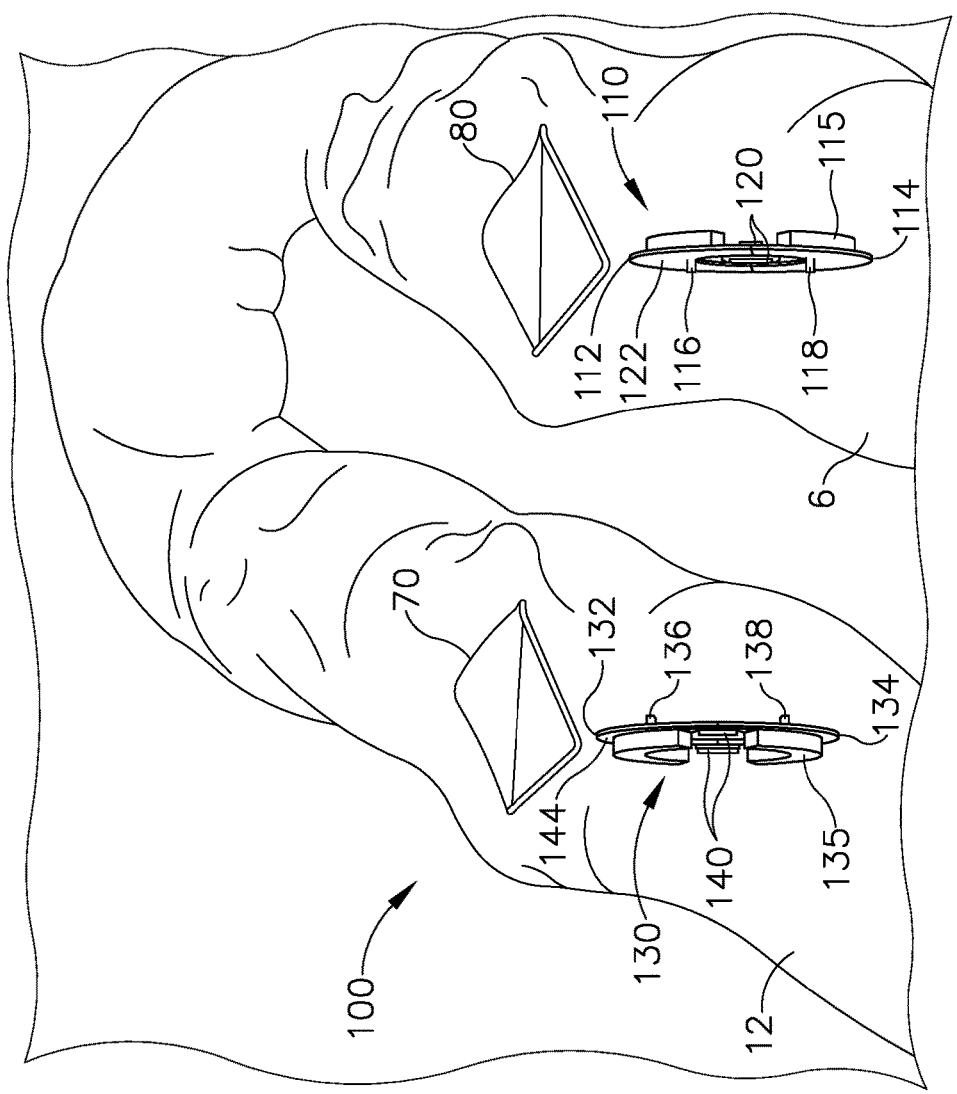
FIG. 8A depicts a perspective view of a patient's digestive system during an anastomosis procedure, with the portions of the anastomosis compression device of FIG. 3A approaching enterotomies formed in different portions of the patient's small intestine for insertion.
Figure 8B:
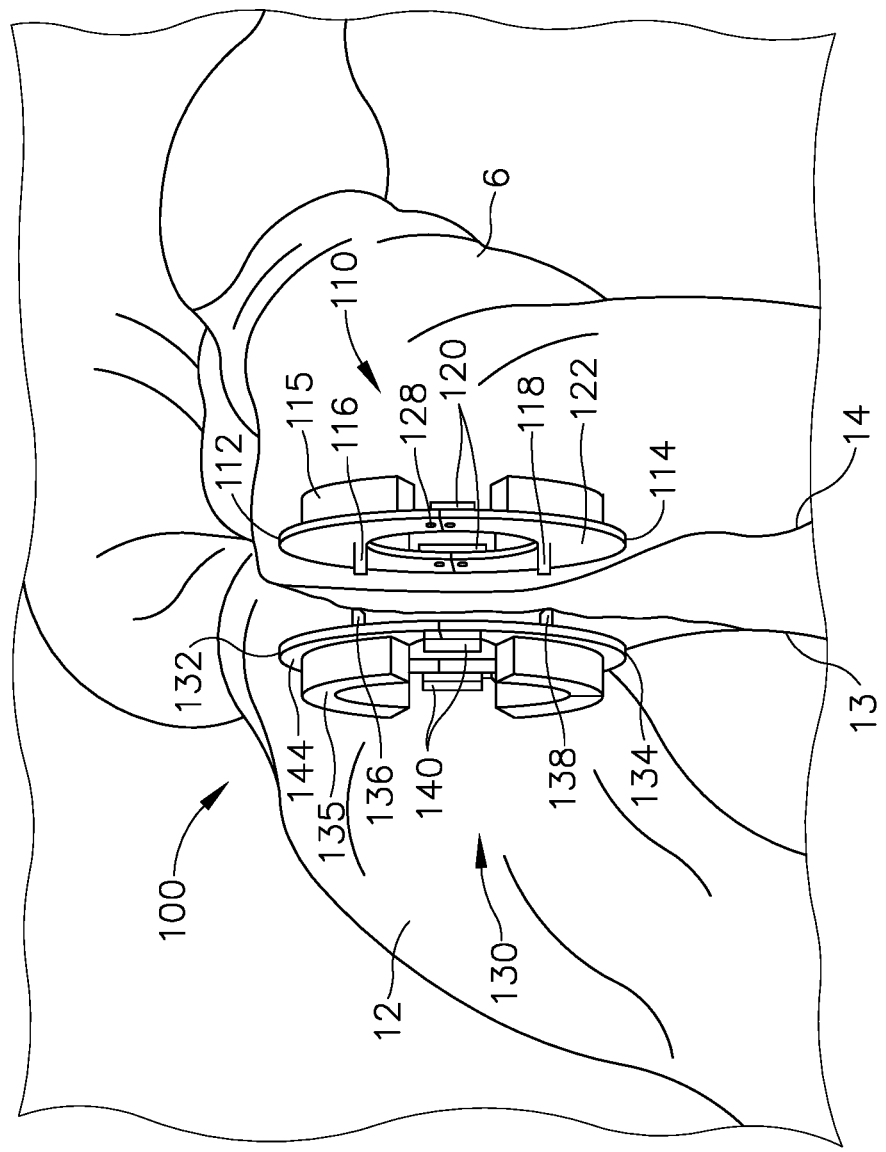
FIG. 8B depicts a perspective view of a patient's digestive system during the anastomosis procedure of FIG. 8A, with portion of tissue omitted to show the portions of the anastomosis compression device in position and urged toward each other to thereby urge the portions of the patient's small intestine toward each other and hold the portions together to form an anastomosis.

In another example where the connection is a side-to-side anastomosis (2), by way of example only and not limitation, the procedure includes forming the anastomosis (2) by mechanical fastening. In this regard, and as shown in FIG. 8A, the procedure involves creating a first enterotomy (70) at the proximal location, creating a second enterotomy (80) at the distal location, and mechanically fastening the first and second enterotomies (70, 80) as shown in FIG. 8B.

By way of further example, and not limitation, in one example the pathway (5) is created within the intestinal tract (9) by forming a first opening (70) in a first hollow organ (11), and forming a second opening (80) in a second hollow organ (11). It should be understood that the first hollow organ and the second hollow organ can be separate organs or different portions of the same organ. By way of example and not limitation, the first and second hollow organs may be different portions of the small intestine. In other examples the first and second hollow organs may be the small intestine and colon respectively. In view of the teachings herein, other examples for the first and second hollow organs will be apparent to those of ordinary skill in the art.

With the first and second openings (70, 80) created, a first portion (110) of the anastomosis compression assembly (100) is inserted into the first opening (70). A second portion (130) is inserted into the second opening (80). To further create the pathway (5), the first and second hollow organs (11) are moved toward each other to align the first portion (110) and second portion (130) with each other. With the first and second portions (110, 130) aligned, their positions are secured relative to each other, and a layer of tissue from each of the first hollow organ (11) and the second hollow organ (11) is compressed in apposition between the secured first and second portions (110, 130) of the anastomosis compression assembly (100).

In one instance of the proceeding example for creating the pathway (5) within the intestinal tract (9), the first opening (70) is formed within the small intestine (11) at a location distal to the duodenal papilla (17), and the second opening (80) is proximal to the ileocecal junction (21). In another instance, the first opening (70) is formed within the small intestine (11) at a location distal to the duodenal papilla (17), and the second opening (80) is distal to the ileocecal junction (21). In yet another instance, the first opening (70) is formed within the jejunum (4) at a location about 100 centimeters (or about one-third the length of the jejunum) distal to the ligament of Treitz (19), and the second opening (80) is formed within the jejunum (4) at a location about 250 centimeters proximal to the ileocecal junction (21). In another instance, the first opening (70) is formed in a proximal portion of the jejunum (4), and the second opening (80) is formed distal to the first opening (70) at a distance between about 10% and about 70% of the length of the small intestine (11).

The above examples and procedures are merely exemplary and various modifications in the locations used or steps performed in creating one or more pathways within the digestive system of a patient will be apparent to those or ordinary skill in the art in view of the teachings herein.

The procedures described above and elsewhere herein may be performed using any of the various devices described below. In addition, or in the alternative, the procedures described above and elsewhere herein may be performed using any of the devices described in U.S. Pat. No. 8,828,031, entitled "Apparatus for Forming an Anastomosis," issued Sep. 9, 2014, the disclosure of which is incorporated by reference herein; U.S. Pat. No. 8,828,032, entitled "Methods and Apparatus for Magnet-Induced Compression Anastomosis Between Adjacent Organs," issued Sep. 9, 2014, the disclosure of which is incorporated by reference herein; U.S. Pat. No. 7,445,622, entitled "Anastomotic Ring Applier with Double Motion Actuation," issued Nov. 4, 2008, the disclosure of which is incorporated by reference herein; U.S. Pat. No. 8,142,454, entitled "Apparatus and Method for Magnetic Alteration of Anatomical Features," issued Mar. 27, 2012, the disclosure of which is incorporated by reference herein; U.S. Pat. No. 6,171,320, entitled "Surgical Clip," issued Jan. 9, 2001, the disclosure of which is incorporated by reference herein; U.S. Pat. No. 8,870,899, entitled "Self-Assembling Magnetic Anastomosis Device Having an Exoskeleton," issued Oct. 28, 2014, the disclosure of which is incorporated by reference herein; U.S. Pat. No. 7,780,686, entitled "Anastomotic Device," issued Aug. 24, 2010, the disclosure of which is incorporated by reference herein; U.S. Pat. No. 7,637,919, entitled "Anastomosis System for Performing Anastomosis in Body," issued Dec. 29, 2009, the disclosure of which is incorporated by reference herein; U.S. Pat. No. 8,197,498, entitled "Gastric Bypass Devices and Procedures," issued Jun. 12, 2012, the disclosure of which is incorporated by reference herein; U.S. Pat. No. 9,381,041, entitled "Methods and Devices for Access Across Adjacent Tissue Layers," issued Jul. 5, 2016, the disclosure of which is incorporated by reference herein; U.S. Pat. No. 8,864,781, entitled "Intestinal Bypass Using Magnets," issued Oct. 21, 2014, the disclosure of which is incorporated by reference herein; U.S. Pat. No. 8,684,995, entitled "Treatment Method," issued Apr. 1, 2014, the disclosure of which is incorporated by reference herein; U.S. Pat. No. 9,456,820, entitled "Incisionless Gastric Bypass Method and Devices," issued Oct. 4, 2016, the disclosure of which is incorporated by reference herein; U.S. Pub. No. 2011/0137394, entitled "Methods and Systems for Penetrating Adjacent Tissue Layers," published Jun. 9, 2011, now abandoned, the disclosure of which is incorporated by reference herein; U.S. Pub. No. 2007/0142850, entitled "Compression Anastomosis Device," published Jun. 21, 2007, now abandoned, the disclosure of which is incorporated by reference herein; U.S. Pub. No. 2006/0036267, entitled "Methods and Apparatus for Performing Malabsorptive Bypass Procedures within a Patient's Gastro-Intestinal Lumen," published Feb. 16, 2006, now abandoned, the disclosure of which is incorporated by reference herein; U.S. Provisional Patent App. No. 61/697,845, entitled "Magnetic Compression Anastomosis Device," filed Sep. 7, 2012, the disclosure of which is incorporated by reference herein; U.S. Pat. No. 9,364,238, entitled "Method and Apparatus for Joining Hollow Organ Sections in Anastomosis," issued Jun. 14, 2016, the disclosure of which is incorporated by reference herein; U.S. patent application Ser. No. 15/298,816, entitled "Method for Partial Diversion of the Intestinal Tract," filed Oct. 20, 2016, published as U.S. Pub. No. 2017/0035425 on February 9, 2017, the disclosure of which is incorporated by reference herein; the journal article entitled "Endoscopic Intestinal Bypass Creation by Using Self-Assembling Magnets in a Porcine Model," by Dr. Marvin Ryou et al., from Gastrointestinal Endoscopy, Vol. 83, No. 4, pp. 821-25, 2016; and/or the journal article entitled "Minimally Invasive Entero-Enteral Dual-Path Bypass Using Self-Assembling Magnets," by Dr. Marvin Ryou et al., from Surgical Endoscopy, published online by Springer Feb. 19, 2016. Still other devices that may be used to perform the procedures described herein will be apparent to those of ordinary skill in the art in view of the teachings herein.

II. EXEMPLARY FRAGMENTABLE ANASTOMOSIS COMPRESSION ASSEMBLIES AND ASSOCIATED METHODS OF USE

In some instances, it may be desirable to provide an anastomosis compression assembly that is capable of breaking apart within the gastrointestinal tract after the anastomosis is formed. When an anastomosis compression assembly breaks apart into pieces or segments, the broken-up anastomosis compression assembly may travel through the remainder of the gastrointestinal tract more easily. For instance, a broken-up anastomosis compression assembly may travel more easily through the ileocecal junction (21) more easily than a fully intact anastomosis compression assembly.

The following description provides examples of various anastomosis compression assemblies that are configured to break apart within the gastrointestinal tract after the anastomosis compression assemblies form an anastomosis. It should be understood that the anastomosis devices described below may be used in any of the various anastomosis procedures described above and in any of the various anastomosis procedures described in the various references described herein. Other suitable ways in which the below-described anastomosis devices may be used will be apparent to those of ordinary skill in the art in view of the teachings herein.

While the devices described below are described in the context of a side-to-side anastomosis, it should be understood that the devices may alternatively be used to provide an end-to-end anastomosis (e.g., to join the severed ends of two portions of a patient's gastrointestinal tract). Various suitable ways in which the devices described below may be used to provide an end-to-end anastomosis will be apparent to those of ordinary skill in the art in view of the teachings herein.

A. Exemplary Fragmentable Anastomosis Compression Disc Assembly

Figure 3A:
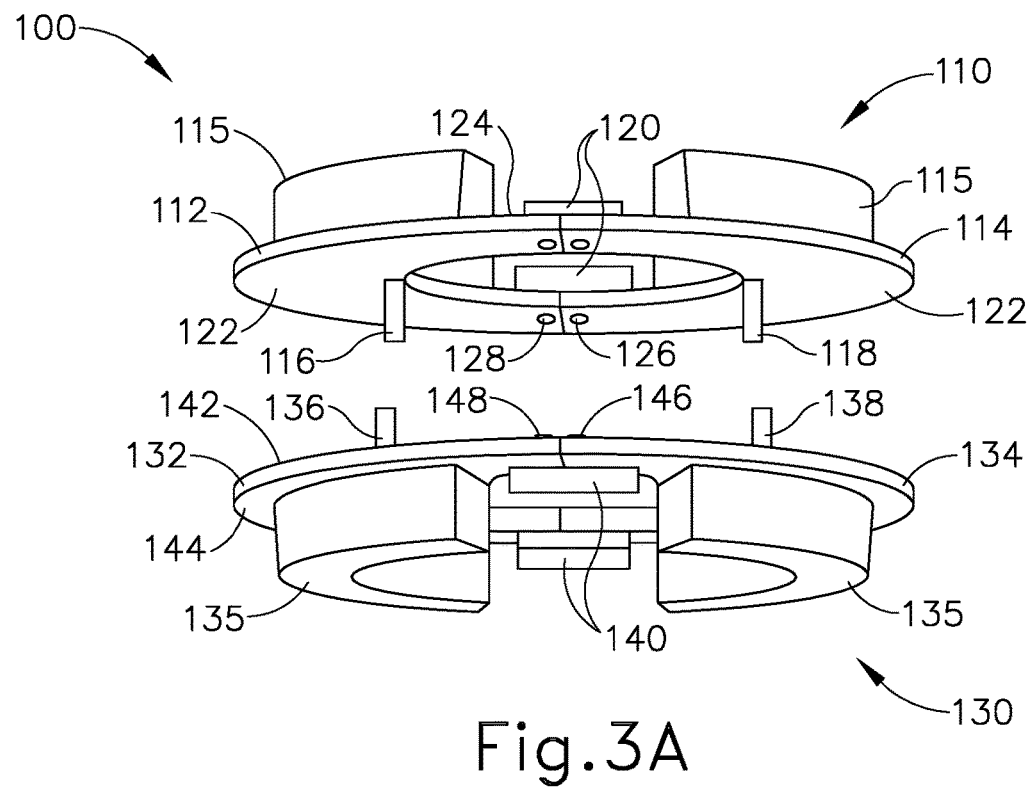
FIG. 3A depicts a perspective view of an exemplary anastomosis compression device, with two device portions in a separated state.
Figure 3B:
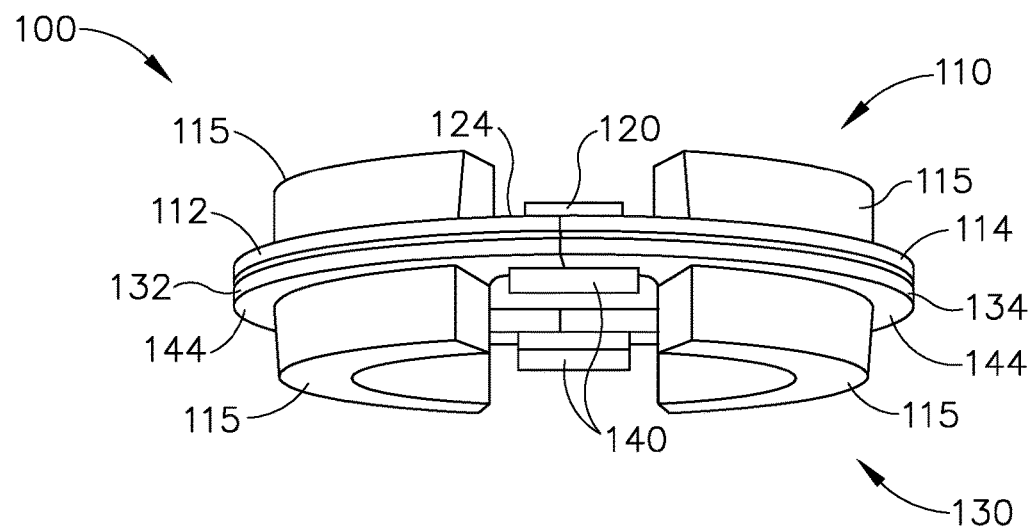
FIG. 3B depicts a perspective view of the anastomosis compression device of FIG. 3A, with the two device portions in an assembled state.

FIGS. 3A-3B show an exemplary fragmentable anastomosis compression assembly (100). Fragmentable anastomosis compression assembly (100) of the present example comprises a first portion (110) and a second portion (130) that are configured to be coupled together along inner surfaces (122, 142). First portion (110) comprises a first segment (112) and a second segment (114) securely coupled together along edges (126) by a pair of joining members (120). First segment (112) includes a body (115) extending distally from an outer surface (124) and an interlocking mechanism (116) extending distally from an inner surface (122). Second segment (114) includes a body (115) extending distally from an outer surface (124) and an interlocking mechanism (118) extending distally from an inner surface (122). Similarly, second portion (130) comprises a first segment (132) and a second segment (134) securely coupled together along edges (146) by a pair of joining members (140). First segment (132) includes a body (135) extending distally from an outer surface (144) and an interlocking mechanism (136) extending distally from an inner surface (142). Second segment (134) includes a body (135) extending distally from an outer surface (144) and an interlocking mechanism (138) extending distally from an inner surface (142).

Figure 4:
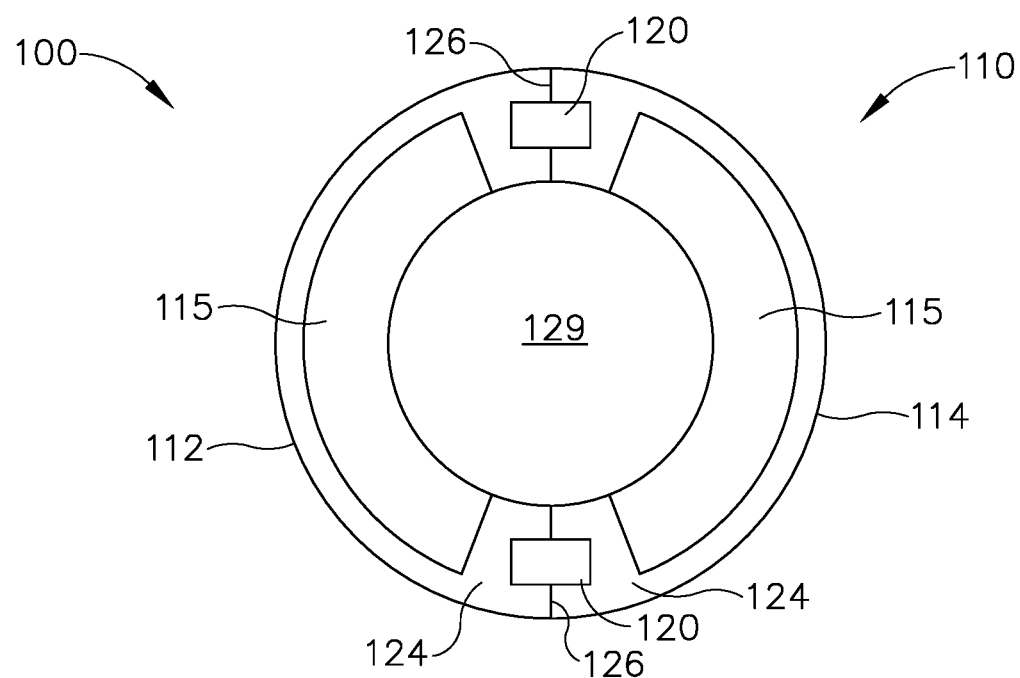
FIG. 4 depicts a top plan view of the anastomosis compression device of FIG. 3A, in the assembled state.

In the present example, as best seen in FIG. 4, first segment (112) and second segment (114) of first portion (110) each define a semi-circular shape with a cavity (129). When first segment (112) and second segment (114) of first portion (110) are coupled together along edges (126) by a pair of joining members (120), the segments (112, 114) create a complete circular shape with cavity (129) enclosed by the boundaries of segments (112, 114). Joining members (120) are positioned along contacting edges (126) of first segment (112) and second segment (114) when brought together to thereby securely affix segments (112, 114) into first portion (110). As shown in FIG. 4, joining members (120) are positioned along an outer surface (124) of first portion (110) and may comprise multiple joining members (120). Although two joining members (120) are displayed in the exemplary version, it should be understood that more or fewer joining members (120) may be included in first portion (110).

Figure 5:
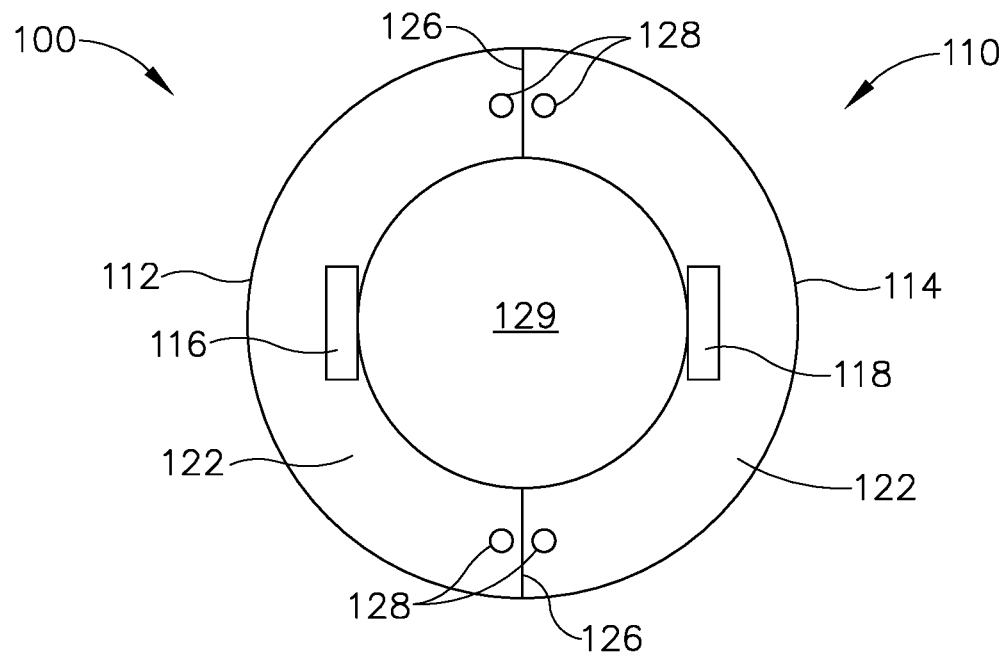
FIG. 5 depicts a bottom plan view of the anastomosis compression device of FIG. 3A, in the assembled state.
Figure 6:
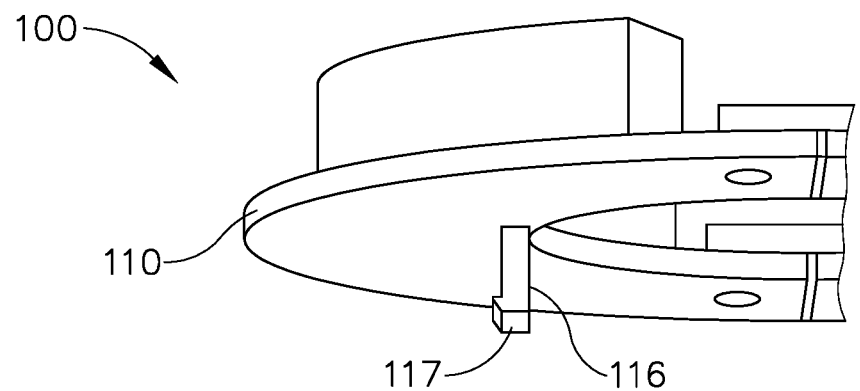
FIG. 6 depicts a partial perspective view of the anastomosis compression device of FIG. 3A, with the interlocking mechanism of the top portion including a latch.

As best seen in FIG. 5, joining members (120) securely attach first segment (112) and second segment (114) of first portion (110) along edges (126) through pins (128). Although not shown, it should be understood that joining members (120) may be securely attached to first portion (110) through some means other than pins (128) as will be apparent to those of ordinary skill in the art. Joining members (120) each have a cross-sectional area that is less than the cross-sectional area of first segment (112) and second segment (114) of first portion (110).

FIG. 4 shows a body (115) of first segment (112) and second segment (114) similarly positioned along outer surface (124) of first portion (110). Body (115) defines an semi-circular shape that is analogous to that of first segment (112) and second segment (114) of first portion (110). Body (115) of first segment (112) and second segment (114) comprises an area along outer surface (124) of first segment (112) and second segment (114) less than the total surface area of segments (112, 114) to accommodate area for joining members (120) on outer surface (124). Therefore, when first segment (112) and second segment (114) of first portion (110) are securely attached to each other by joining members (120) along edges (126), body (115) of first segment (112) does not contact body (115) of second segment (114).

As further seen in FIG. 5, first segment (112) and second segment (114) of first portion (110) each include interlocking mechanisms (116, 118) extending distally from an inner surface (122). Interlocking mechanisms (116, 118) of first portion (110) comprise a latch (117) to thereby allow first portion (110) to securely attach to a second portion (130) upon an operator's application of force urging portions (110, 130) toward each other. By way of example only, interlocking mechanisms (116, 118) of first portion (110) may each comprise a latch, some other kind of fastener, features configured to provide a snap fit, or some other kind of engaging mechanism as would be apparent to one of ordinary skill in the art.

Similarly, as best seen in FIGS. 3A-3B, first segment (132) and second segment (134) of second portion (130) each define a semi-circular shape with a cavity (129). Analogous to first portion (110), when first segment (132) and second segment (134) of second portion (130) are coupled together along edges (146) by a pair of joining members (140), the segments (132, 134) create a complete circular shape with cavity (149) enclosed by the boundaries of segments (132, 134). Joining members (140) are positioned along the contacting edges (146) of first segment (132) and second segment (134) when brought together to thereby securely affix the segments (132, 134) into second portion (130).

As identically shown in FIG. 4 for first portion (110), joining members (140) of second portion (130) are positioned along outer surface (144) and may comprise multiple joining members (140). Although two joining members (140) are displayed in the exemplary version displayed in FIG. 3A, it should be understood that more or fewer joining members (140) may be included in second portion (130). As identically shown in FIG. 5 for first portion (110), joining members (140) of second portion (130) securely attach first segment (132) and second segment (134) of second portion (130) along edges (146) through pins (148). Although not shown, it should be understood that joining members (140) may be securely attached to second portion (130) through some means other than pins (148) as will be apparent to those of ordinary skill in the art. Joining members (140) each have a cross-sectional area that is less than the cross-sectional area of first segment (132) and second segment (134) of second portion (130).

FIGS. 3A-3B show body (135) of first segment (132) and second segment (134) similarly positioned along outer surface (144) of second portion (130). Body (135) includes a semi-circular shape that is analogous to that of first segment (132) and second segment (134) of second portion (130). Body (135) of first segment (132) and second segment (134) has an area along outer surface (144) that is less than the total surface area of first segment (132) and second segment (134) to accommodate area for joining members (140) on outer surface (144). Therefore, when first segment (132) and second segment (134) of second portion (130) are securely attached to each other by joining members (140) along edges (146), body (135) of first segment (132) does not contact body (135) of second segment (134).

Figure 7:
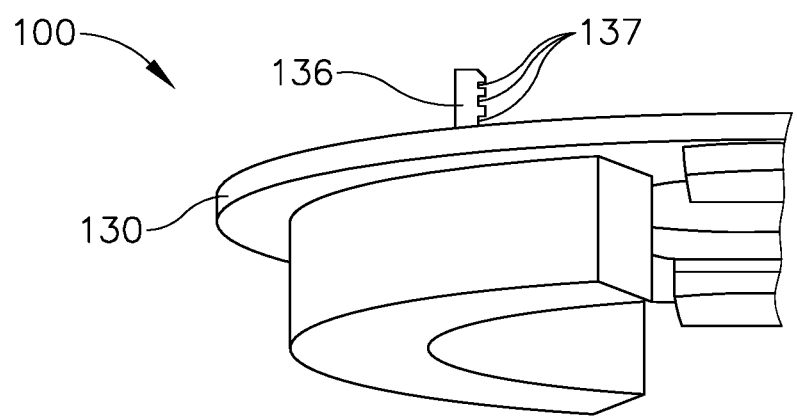
FIG. 7 depicts a partial perspective view of the anastomosis compression device of FIG. 3A, with the interlocking mechanism of the bottom portion including receiver slots.

First segment (132) and second segment (134) of second portion (130) each further include interlocking mechanisms (136, 138) extending distally from inner surface (142). As best seen in FIG. 7, interlocking mechanisms (136, 138) of second portion (130) comprise one or more slots (137) to thereby allow second portion (130) to securely attach to the interlocking mechanisms (116, 118) of first portion (110) upon an operator's application of force urging portions (110, 130) toward each other. By way of example only, interlocking mechanisms (136, 138) of second portion (130) may comprise a single catch, multiple receiving slots, or other engaging mechanism as would be apparent to one of ordinary skill in the art. Other suitable ways in which first portion (110) and second portion (130) of anastomosis compression assembly (100) may be securely attached will be apparent to those of ordinary skill in the art in view of the teachings herein.

In the present example, first segments (112, 132) and second segments (114, 134) of first and second portions (110, 130) are formed of a nondegradable material. Similarly, bodies (115, 135) and interlocking mechanisms (116, 118, 136, 138) of first and second portions (110, 130) are configured to be nondegradable when inserted into the gastrointestinal tract or other lumen within a patient's body. Various suitable nondegradable materials that may be used for anastomosis compression assembly (100) will be apparent to those of ordinary skill in the art in view of the teachings herein.

Joining members (120, 140) and pins (128, 148) of first portion (110) and second portion (130) are formed of a degradable material to thereby allow for their degradation when inserted into the gastrointestinal tract or other lumen within a patient's body. In some versions, joining members (120, 140) and pins (128, 148) of portions (110, 130) comprise polydioxanone (PDS). Other suitable degradable materials that may be used to form joining members (120, 140) and pins (128, 148) will be apparent to those of ordinary skill in the art in view of the teachings herein. Joining members (120, 140) and pins (128, 148) are configured to be biodegradable to thereby allow fragmentation of anastomosis compression assembly (100) into smaller pieces, after a predetermined amount of time in a patient's gastrointestinal tract or other area, in order to ease the fluid passage of the anastomosis compression assembly (100) through the remainder of the gastrointestinal tract after the target site of the anastomosis (2) has effectively necrosed.

Although not shown, it should be understood that first segments (112, 132) and second portions (114, 134) of first and second portions (110, 130) may comprise shapes other than the semi-circular configurations displayed in the exemplary version. In addition, bodies (115, 135) of portions (110, 130) may also comprise configurations varied from the semi-circular shapes shown in the exemplary version. Various suitable dimensions and other structural configurations that may be used for anastomosis compression assembly (100) will be apparent to those of ordinary skill in the art in view of the teachings herein.

B. Exemplary Anastomosis Procedure Using Exemplary Fragmentable Anastomosis Compression Disc Assembly In a side-to-side anastomosis (2), the procedure includes forming an anastomosis (2) by compression of tissue through the use of an exemplary anastomosis compression assembly (100). Referring to FIG. 8A, in such procedures a first portion (110) of anastomosis compression assembly (100) is introduced into a patient's first lumen (for exemplary purposes, an ileum (6)) through an enterotomy (80); and a second portion (130) of anastomosis compression assembly (100) is introduced into a patient's second lumen (for exemplary purposes, a duodenum (12)) through another enterotomy (70). First portion (110) includes an outer surface (122) that mates with, or is configured to be oriented adjacent to, a corresponding outer surface (142) on second portion (130).

As seen in FIG. 8B, the procedure further includes moving first portion (110) and second portion (130) of anastomosis compression assembly (100) toward each other. Once first portion (110) and second portion (130) are aligned with one another, an operator may compress first lumen wall (13) at the first attachment region where first portion (110) is positioned and a second lumen wall (14) at the second attachment region where second portion (130) is positioned.

Figure 8C:
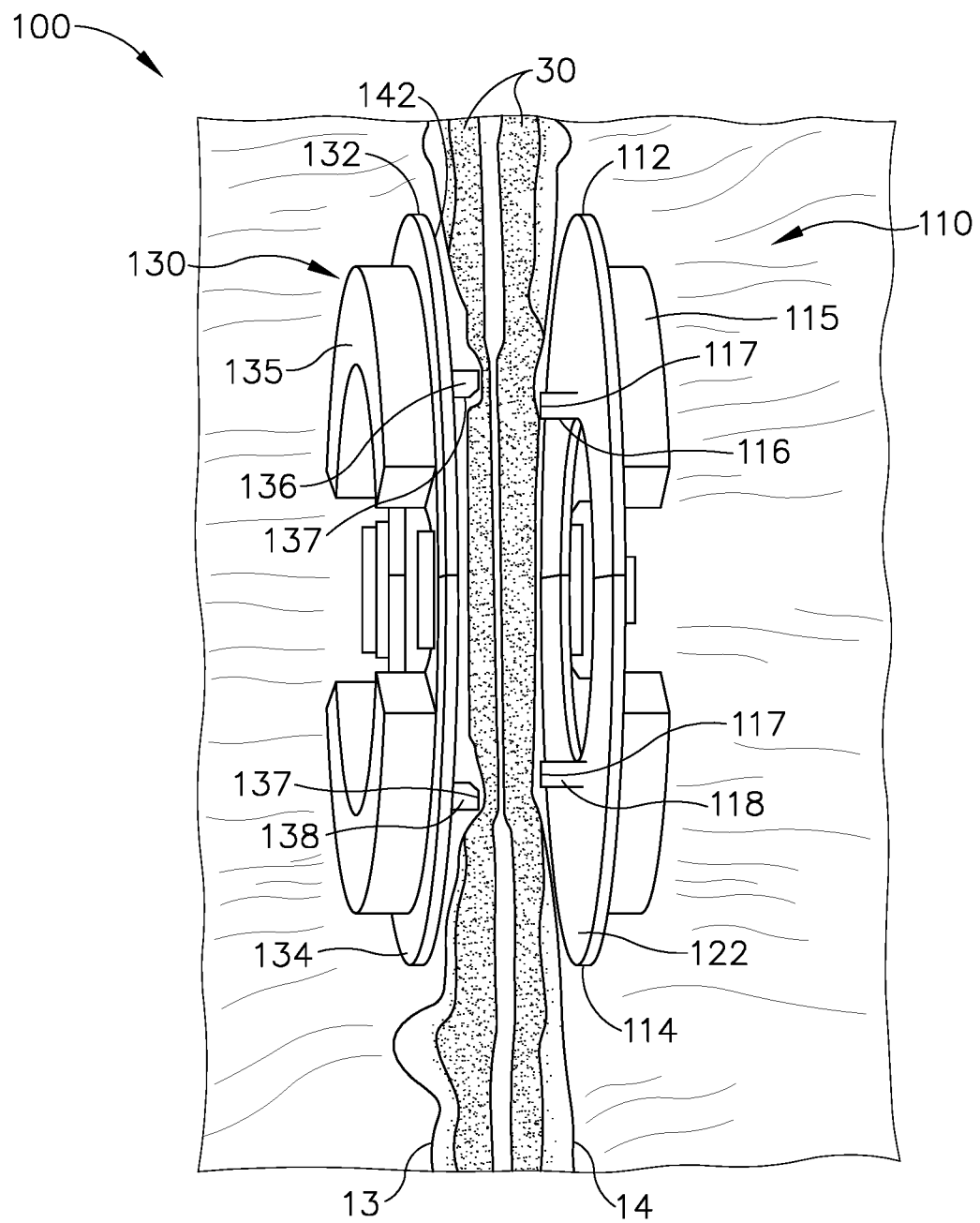
FIG. 8C depicts a cross-sectional view of the portions of the anastomosis compression device of FIG. 3A opposingly positioned in a patient's small intestine, with live tissue positioned between opposing surfaces of the anastomosis compression device portions.

As best seen in FIG. 8C, between outer surface (122) of first portion (110) and outer surface (142) of second portion (130) of the exemplary anastomosis compression assembly (100) is a layer of tissue (30) from each of the first lumen wall (13) and the second lumen wall (14). Compression upon body (115) of first portion (110) and body (135) of second portion (130) of the anastomosis compression assembly (100) correspondingly compresses against the captured tissue (30). Joining members (120) of first portion (110) and joining members (140) of second portion (130) maintain their structure and composition and remain fully intact despite their initial exposure to the lumens of the patient's body. By compressing portions (110, 130) toward each other, interlocking mechanism (116) of first portion (110) is urged toward corresponding interlocking mechanism (136) of second portion (130); and interlocking mechanism (118) of first portion (110) is urged toward corresponding interlocking mechanism (138) of second portion (130). Interlocking mechanisms (116, 118) remain within lumen wall (14) and interlocking mechanisms (136, 138) remain within lumen wall (13) until the force applied exceeds the tensile strength of lumen walls (13, 14). Latches (117) of interlocking mechanisms (116, 118) pierce through lumen wall (14) as a result, and corresponding slots (137) of interlocking mechanisms (136, 138) pierce through lumen wall (13), thereby allowing interlocking mechanisms (116, 118) of first portion (110) to engage and fasten with interlocking mechanisms (136, 138) of second portion (130). This engagement secures first portion (110) relative to second portion (130) and vice-versa.

Figure 8D:
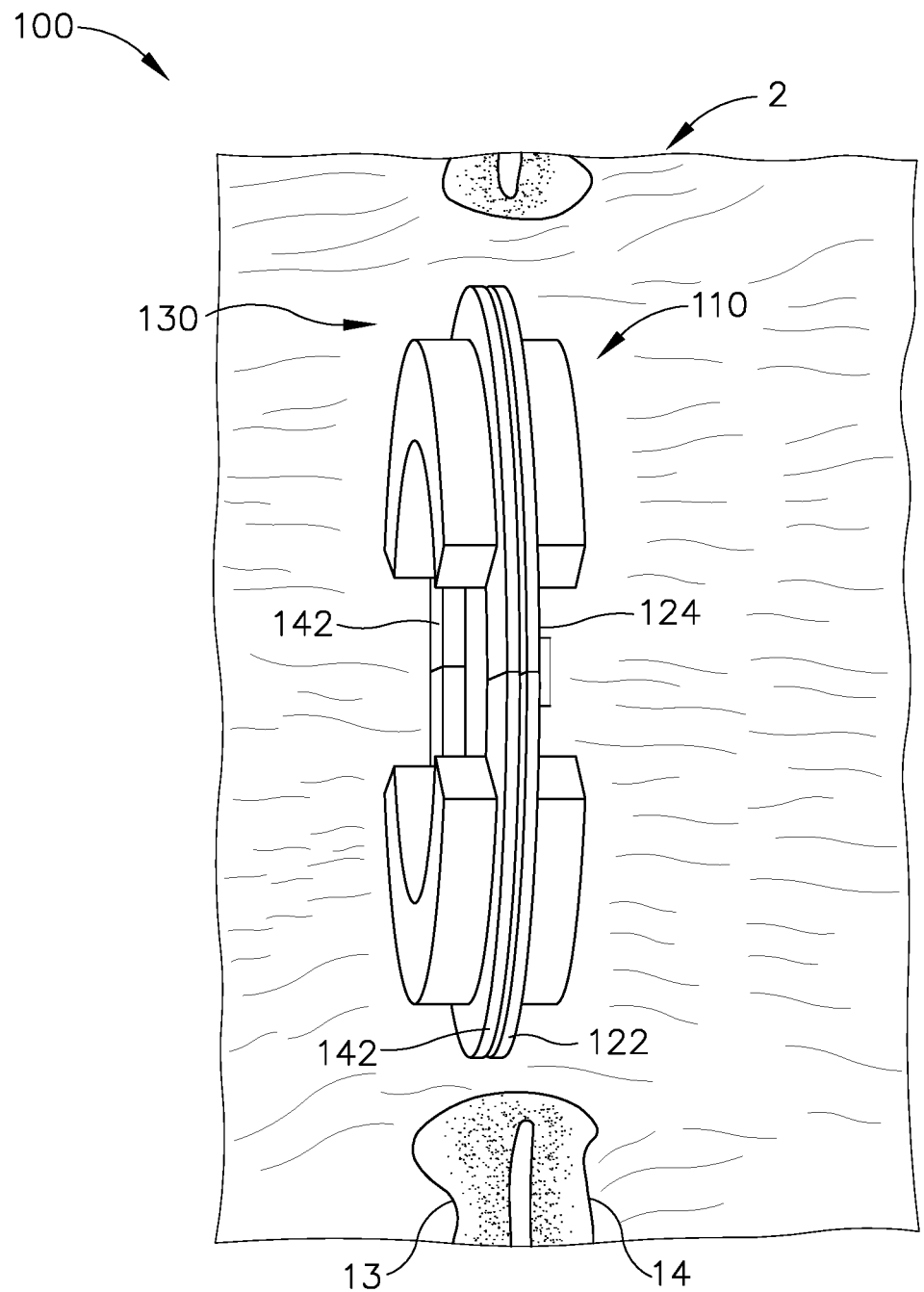
FIG. 8D depicts a cross-sectional view of the portions of the anastomosis compression device of FIG. 3A opposingly positioned in the patient's small intestine, with the tissue positioned between the opposing surfaces of the anastomosis compression portions in a state of necrosis, with the biodegradable joining members connecting the segments of the anastomosis compression device portions having degraded.

Over a period of time, the ischemia caused by the compression of tissue (30) between first portion (110) and second portion (130) of anastomosis compression assembly (100) eventually results in necrosis of the tissue (30), as shown in FIG. 8D. This necrosis eventually reaches a point where lumen walls (13, 14) can no longer structurally support anastomosis compression assembly (100) such that anastomosis compression assembly (100) breaks free from the site of the anastomosis (2). First portion (110) and second portion (130) of anastomosis compression assembly (100) remain held together though the engagement of interlocking mechanisms (116, 118) of first portion (110) and interlocking mechanisms (136, 138) of second portion (130) so that inner surface (122) of first portion (110) and inner surface (142) of second portion (130) are securely pressed against each other.

Figure 8E:
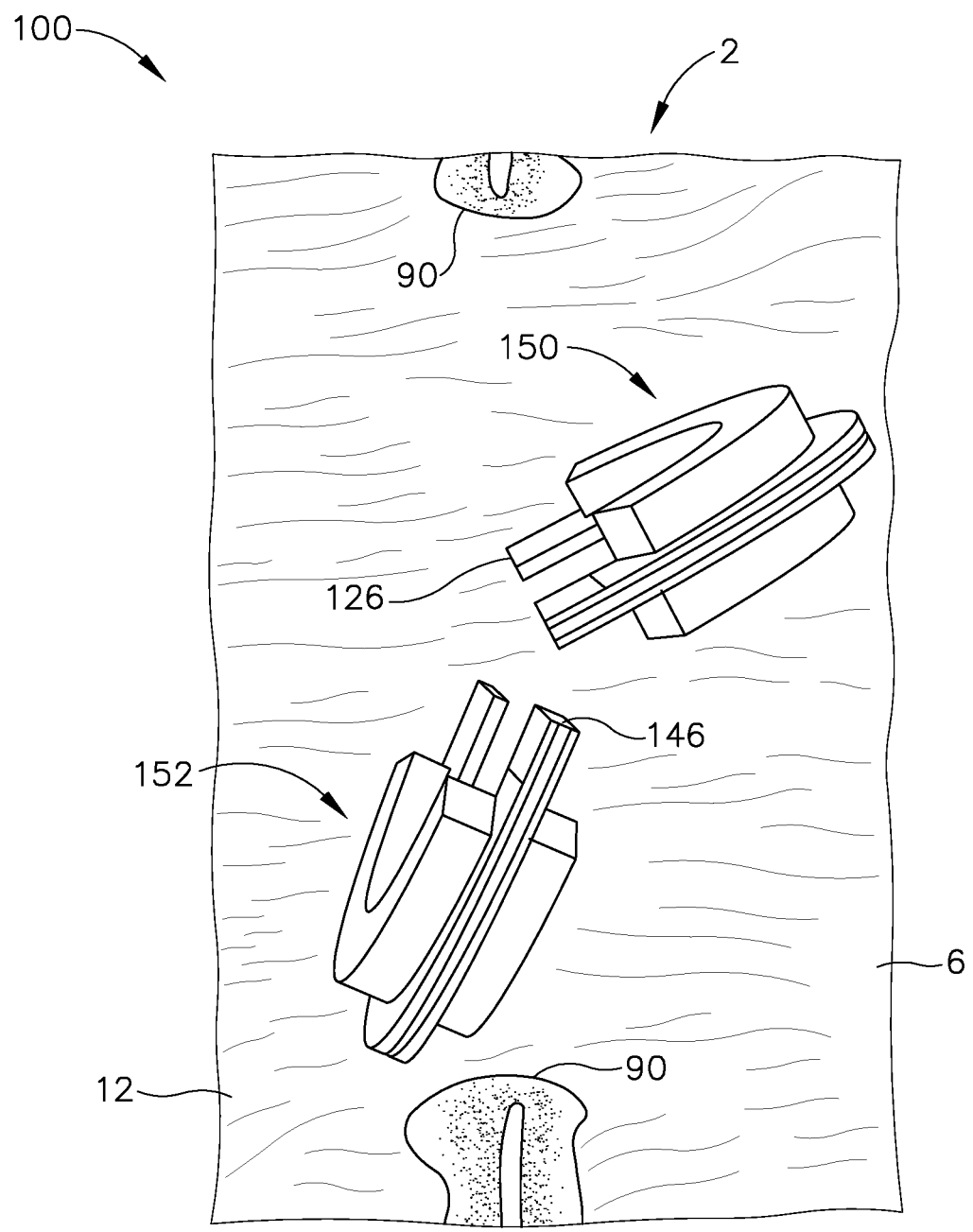
FIG. 8E depicts a cross-sectional view of the portions of the anastomosis compression device of FIG. 3A, with the anastomosis compression device portions breaking into smaller segments after the degradation of the biodegradable joining members, with the segments beginning to leave the anastomosis formed between the portions of the patient's small intestine and pass through the remainder of the patient's digestive system while leaving behind a secure anastomosis.

Since anastomosis compression assembly (100) has now been exposed to the gastrointestinal tract of the patient's body for an amount of time in excess of the predetermined tolerable amount by joining members (120) of first portion (110) and joining members (140) of second portion (130), joining members (120, 140) have degraded and are no longer fixed at their original positions along outer surface (124) of first portion (110) and outer surface (144) of second portion (130). Due to this, anastomosis compression assembly (100) no longer maintains structural support along edges (126, 146), thus causing anastomosis compression assembly (100) to fragment into a first half (150) and a second half (152), as seen in FIG. 8E.

The segments (112, 132) of first portion (110) and second portion (130) comprising first half (150) remain held together due to the engagement of interlocking mechanisms (116, 136). Similarly, and the segments (114, 134) of first portion (110) and second portion (130) comprising second half (152) remain held together due to the engagement of interlocking mechanisms (118, 138). First half (150) and second half (152) of anastomosis compression assembly (100) will then pass into the ileum (6) and eventually pass into the bowels and out from the patient with feces. When anastomosis compression assembly (100) leaves the site of the anastomosis (2), the structural integrity of the anastomosis (2) remains secure due to natural tissue adhesions. In particular, the exterior of the duodenum (12) and the ileum (6) may have substantial serosa-to-serosa adhesion at this point, due to the sustained contact between the duodenum (12) and the ileum (6). In addition, the mucosa at the interior of the duodenum (12) and the ileum (6) may have remodeled itself to provide a smooth mucosal transition (90) between the duodenum (12) and the ileum (6) at the site of the anastomosis (2), as shown in FIG. 8E. With the anastomosis (2) complete, chyme may freely pass from the duodenum (12) to the ileum (6) via the anastomosis (2), without needing to pass through the jejunum (4).

C. Exemplary Fragmentable Anastomosis Compression Ring Assembly

Figure 9:
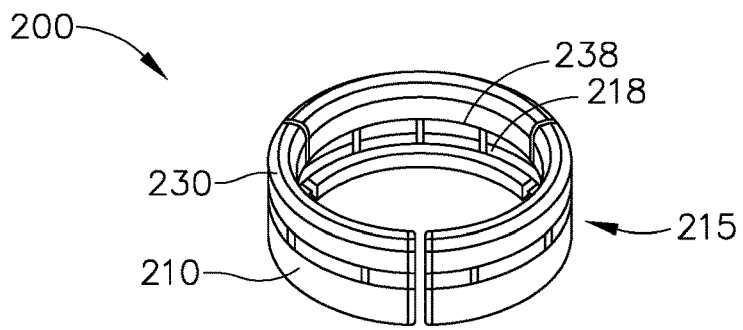
FIG. 9 depicts a perspective view of an exemplary alternative anastomosis compression device, with two portions in an assembled state.
Figure 10:
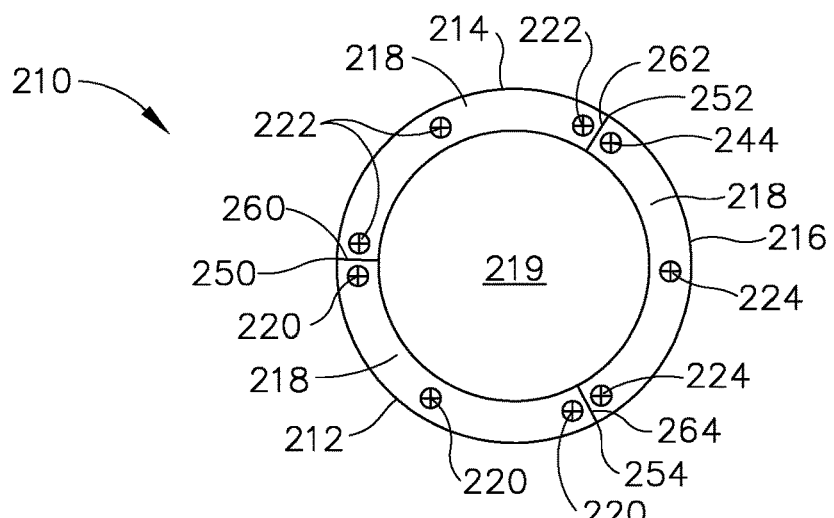
FIG. 10 depicts a top plan view of a first portion of the anastomosis compression device of FIG. 9.

FIG. 9 shows an exemplary segmented anastomotic compression ring (200). Segmented anastomotic compression ring (200) of the present example comprises a first portion (210) and a second portion (230), each comprising a body (215) and configured to be coupled together along inner surfaces (218, 238). As best seen in FIG. 10, first portion (210) comprises a first segment (212), a second segment (214) and a third segment (216) securely coupled together. First segment (212) of first portion (210) is coupled to second segment (214) along edge (250) by a joining member (260). Second segment (214) of first portion (210) is coupled to third segment (216) along edge (252) by a joining member (262). Third segment (216) of first portion (210) is coupled to first segment (212) along edge (254) by a joining member (264). First segment (212) includes an outer surface (124) and interlocking mechanisms (220) extending distally from an inner surface (218) of first portion (210). Second segment (214) includes an outer surface (124) and interlocking mechanisms (222) extending distally from an inner surface (218) of first portion (210). Third segment (216) includes an outer surface (124) and interlocking mechanisms (224) extending distally from an inner surface (218) of first portion (210).

Figure 11:
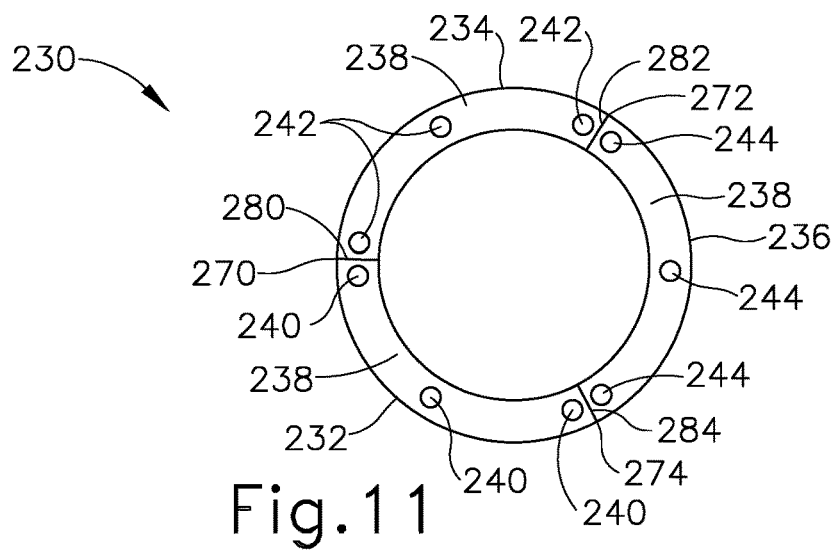
FIG. 11 depicts a bottom plan view of a second portion of the anastomosis compression device of FIG. 9.

Similarly, as seen in FIG. 11, second portion (230) comprises a first segment (232), a second segment (234) and a third segment (236) securely coupled together. First segment (232) of second portion (130) is coupled to second segment (234) along edge (270) by a joining member (280). Second segment (234) of second portion (130) is coupled to third segment (236) of along edge (272) by a joining member (282). Third segment (236) of second portion (130) is coupled to first segment (232) along edge (274) by a joining member (284). First segment (232) includes an outer surface (124) and interlocking mechanisms (240) extending distally from an inner surface (238) of second portion (230). Second segment (234) includes an outer surface (124) and interlocking mechanisms (242) extending distally from an inner surface (238) of second portion (230). Third segment (236) includes an outer surface (124) and interlocking mechanisms (244) extending distally from an inner surface (238) of second portion (230).

In the present example, as best seen in FIG. 10, first segment (212), second segment (214) and third segment (216) of first portion (210) are coupled together along edges (250, 252, 254) by a set of joining members (260, 262, 264) to create a complete circular shape of first portion (210) with cavity (219) enclosed by the boundaries of segments (212, 214, 216). Although one joining member (260) is displayed in the exemplary version between first segment (212) and second segment (214), it should be understood that more joining members (260) may be included along edge (250) to attach first segment (212) to second segment (214). Alternatively, additional links (262) may be provided to securely affix second segment (214) to third segment (216) along edge (252) as will be apparent to those of ordinary skill in the art. Additional links (264) may be included at edge (254) to thereby attach third segment (216) to first segment (212). Joining members (260, 262, 264) each have a cross-sectional area that is less than the cross-sectional area of first segment (212), second segment (214) and third segment (216) of first portion (210).

Figure 12:
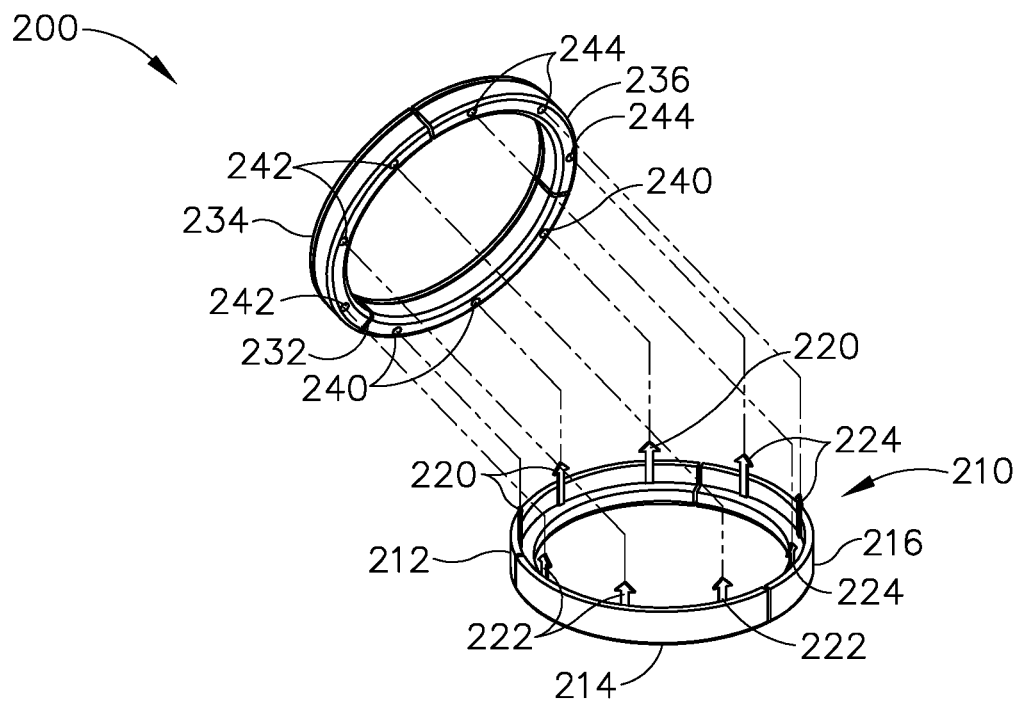
FIG. 12 depicts an exploded perspective view of the anastomosis compression device of FIG. 9, with the first and second portions in a disassembled state.

As further seen in FIG. 12, first segment (212) of first portion (210) includes interlocking mechanisms (220) extending distally from inner surface (218). In the present example, each interlocking mechanism (220) of first portion (210) comprises a needle and thereby allows first segment (212) of first portion (210) to securely attach to first segment (232) of second portion (230) upon an operator's application of force urging portions (210, 230) together. Second segment (214) of first portion (210) includes interlocking mechanisms (222) extending distally from inner surface (218). Each interlocking mechanism (222) of first portion (210) of the present example comprises a needle and thereby allows second segment (214) of first portion (210) to securely attach to second segment (234) of second portion (230) upon an operator's application of force urging portions (210, 230) together. Third segment (216) of first portion (210) includes interlocking mechanisms (224) extending distally from inner surface (218). Each interlocking mechanism (224) of first portion (210) of the present example comprises a needle and thereby allows third segment (216) of first portion (210) to securely attach to third segment (236) of second portion (230) upon an operator's application of force urging portions (210, 230) together. By way of example only, interlocking mechanisms (220, 222, 224) of first portion (210) may comprise a piercing shaft, sharp rod, needle, or other piercing feature that is also capable of providing fastening as would be apparent to one of ordinary skill in the art.

Similar to first portion (210), as best seen in FIG. 11, first segment (232), second segment (234) and third segment (236) of second portion (230) are coupled together along edges (270, 272, 274) by a set of joining members (280, 282, 284) to create a complete circular shape of second portion (230) with cavity (219) enclosed by the boundaries of segments (232, 234, 236). Although one joining member (280) is displayed in the exemplary version between first segment (232) and second segment (234), it should be understood that more joining members (280) may be included along edge (270) to attach first segment (232) to second segment (234). Alternatively, additional links (282) may be provided to securely affix second segment (234) to third segment (236) along edge (272) as will be apparent to those of ordinary skill in the art. Additional links (284) may be included at edge (274) to thereby attach third segment (236) to first segment (232). Joining members (280, 282, 284) each have a cross-sectional area that is less than the cross-sectional area of first segment (232), second segment (234) and third segment (236) of second portion (230).

As further seen in FIGS. 11-12, first segment (232) of second portion (230) includes interlocking mechanisms (240) along inner surface (238). In the present example, interlocking mechanisms (240) comprise receiving slots configured to receive interlocking mechanisms (220) of first segment (212) of first portion (210) to thereby allow first segment (232) of second portion (230) to securely attach to first segment (212) of first portion (210) upon an operator's application of force urging portions (210, 230) together. Second segment (234) of second portion (230) includes interlocking mechanisms (222) along inner surface (238). Interlocking mechanisms (242) of the present example comprise receiving slots configured to receive interlocking mechanisms (222) of second segment (214) of first portion (210) to thereby allow second segment (234) of second portion (230) to securely attach to second segment (214) of first portion (210) upon an operator's application of force urging portions (210, 230) together. Third segment (236) of second portion (230) includes interlocking mechanisms (244) along inner surface (238). Similarly, interlocking mechanisms (244) of the present example comprise receiving slots configured to receive interlocking mechanisms (224) of third segment (216) of first portion (210) to thereby allow third segment (236) of second portion (230) to securely attach to third segment (216) of first portion (210) upon an operator's application of force urging portions (210, 230) together. By way of example only, interlocking mechanisms (240, 242, 244) of second portion (230) may comprise a series of holes, recesses, slots, or other receivers as would be apparent to one of ordinary skill in the art. Other suitable ways in which first portion (210) and second portion (230) of segmented anastomotic compression ring (200) may be securely attached will be apparent to those of ordinary skill in the art in view of the teachings herein.

In the present example, first segments (212, 232), second portions (214, 234) and third portions (216, 236) of first and second portions (210, 230) are formed of a nondegradable material. Similarly, interlocking mechanisms (220, 222, 224) of first portion (210) and interlocking mechanisms (240, 242, 244) of second portion (230) are configured to be nondegradable when inserted into the gastrointestinal tract or other lumen within a patient's body. Various suitable nondegradable materials that may be used for segmented anastomotic compression ring (200) will be apparent to those of ordinary skill in the art in view of the teachings herein.

Joining members (260, 262, 264) of first portion (210) and joining members (280, 282, 284) of second portion (230) are formed of a degradable material to thereby allow for their degradation when inserted into the gastrointestinal tract or other lumen within a patient's body. In some versions, joining members (260, 262, 264) of first portion (210) and joining members (280, 282, 284) of second portion (230) comprise polydioxanone (PDS). Other suitable degradable materials that may be used to form joining members (260, 262, 264, 280, 282, 284) will be apparent to those of ordinary skill in the art in view of the teachings herein. Joining members (260, 262, 264) of first portion (210) and joining members (280, 282, 284) of second portion (230) are configured to be biodegradable to thereby allow for segmentation of anastomotic compression ring (200) into smaller pieces, after a predetermined amount of time in a patient's gastrointestinal tract or other lumen, in order to ease the fluid passage of the anastomotic compression ring (200) through the remainder of the gastrointestinal tract after the target site of the anastomosis (2) has effectively necrosed.

Although not shown, it should be understood that first portion (210) and second portion (230) may comprise shapes other than the circular configurations as displayed in the exemplary version. Various suitable dimensions and other structural configurations that may be used for segmented anastomotic compression ring (200) will be apparent to those of ordinary skill in the art in view of the teachings herein.

Figure 14A:
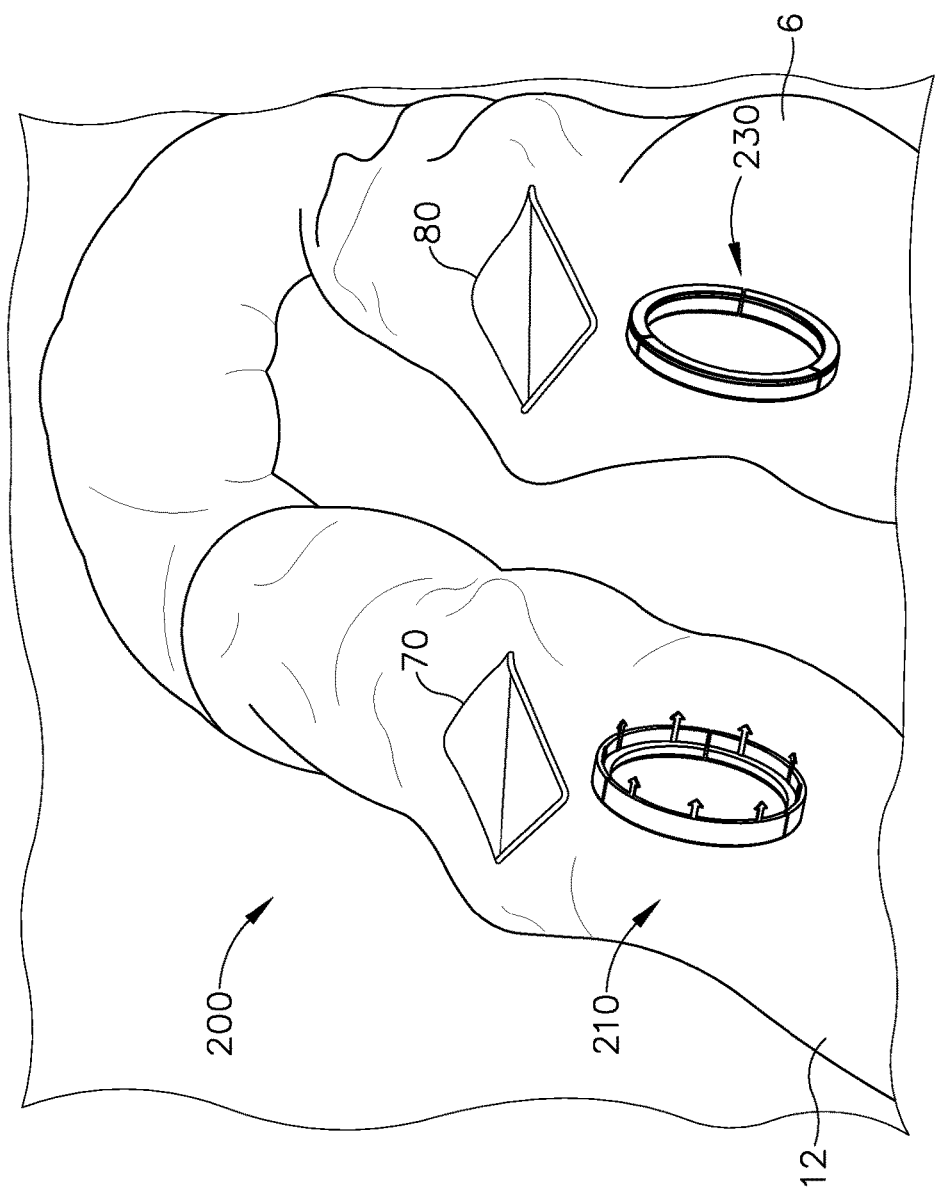
FIG. 14A depicts a perspective view of a patient's digestive system during an anastomosis procedure, with the portions of the anastomosis compression device of FIG. 9 approaching enterotomies formed in different portions of the patient's small intestine for insertion.

D. Exemplary Anastomosis Procedure Exemplary Fragmentable Anastomosis Compression Ring Assembly In a side-to-side anastomosis (2), the procedure includes forming an anastomosis (2) by compression of tissue through the use of an exemplary segmented anastomotic compression ring (200). Referring to FIG. 14A, in such procedures a first portion (210) of anastomotic compression ring (200) is introduced into a patient's first lumen (for exemplary purposes, a duodenum (12)) through an enterotomy (70) and a second portion (230) of anastomotic compression ring (200) is introduced into a patient's second lumen (for exemplary purposes, a ileum (6)) through another enterotomy (80). First portion (210) includes an inner surface (218) that mates with, or is configured to be oriented adjacent to, a corresponding inner surface (238) on second portion (230).

Figure 14B:
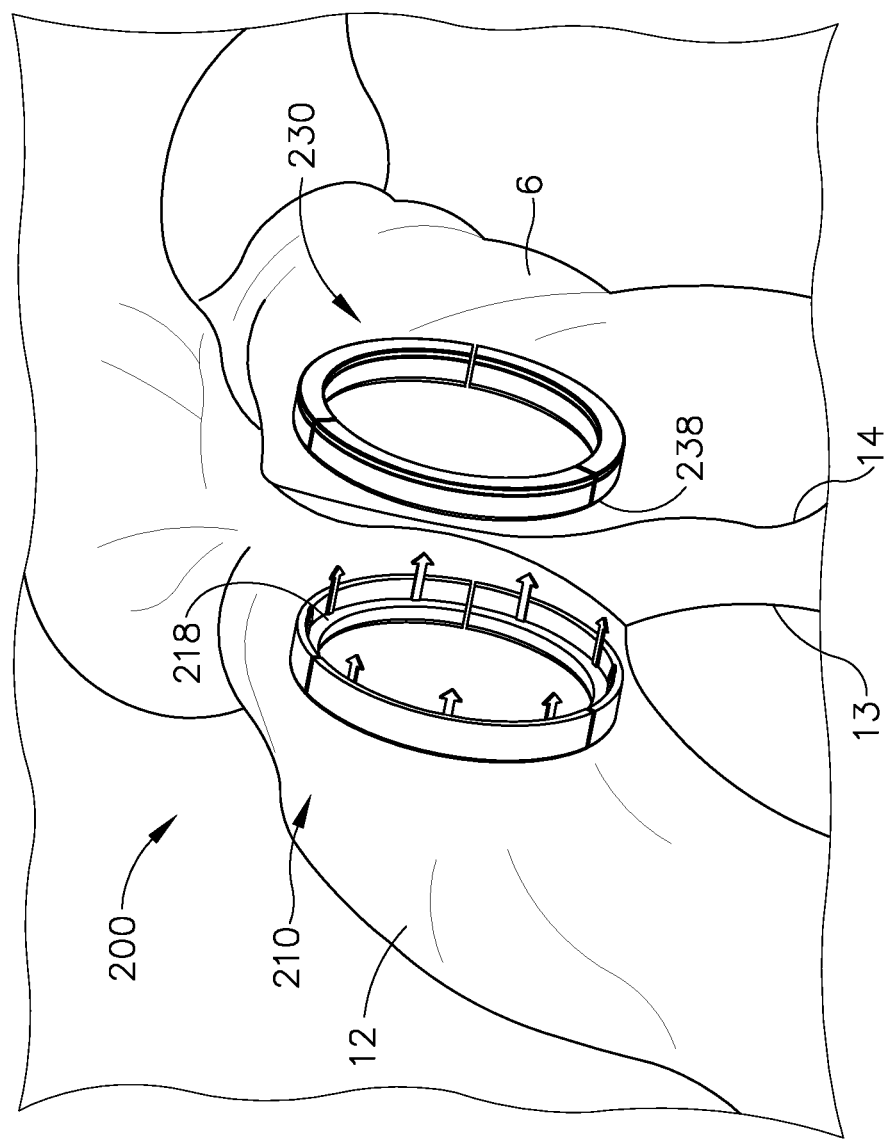
FIG. 14B depicts a perspective view of a patient's digestive system during the anastomosis procedure of FIG. 14A, with portion of tissue omitted to show the portions of the anastomosis compression device in position and urged toward each other to thereby urge the portions of the patient's small intestine toward each other and hold the portions together to form an anastomosis.

As seen in FIG. 14B, the procedure further includes moving first portion (210) and second portion (230) of anastomotic compression ring (200) towards each other. Once first portion (210) and second portion (230) are aligned with one another, an operator may compress a first lumen wall (13) at the first attachment region where first portion (210) is positioned towards a second lumen wall (14) at the second attachment region where second portion (130) is positioned.

Figure 14C:
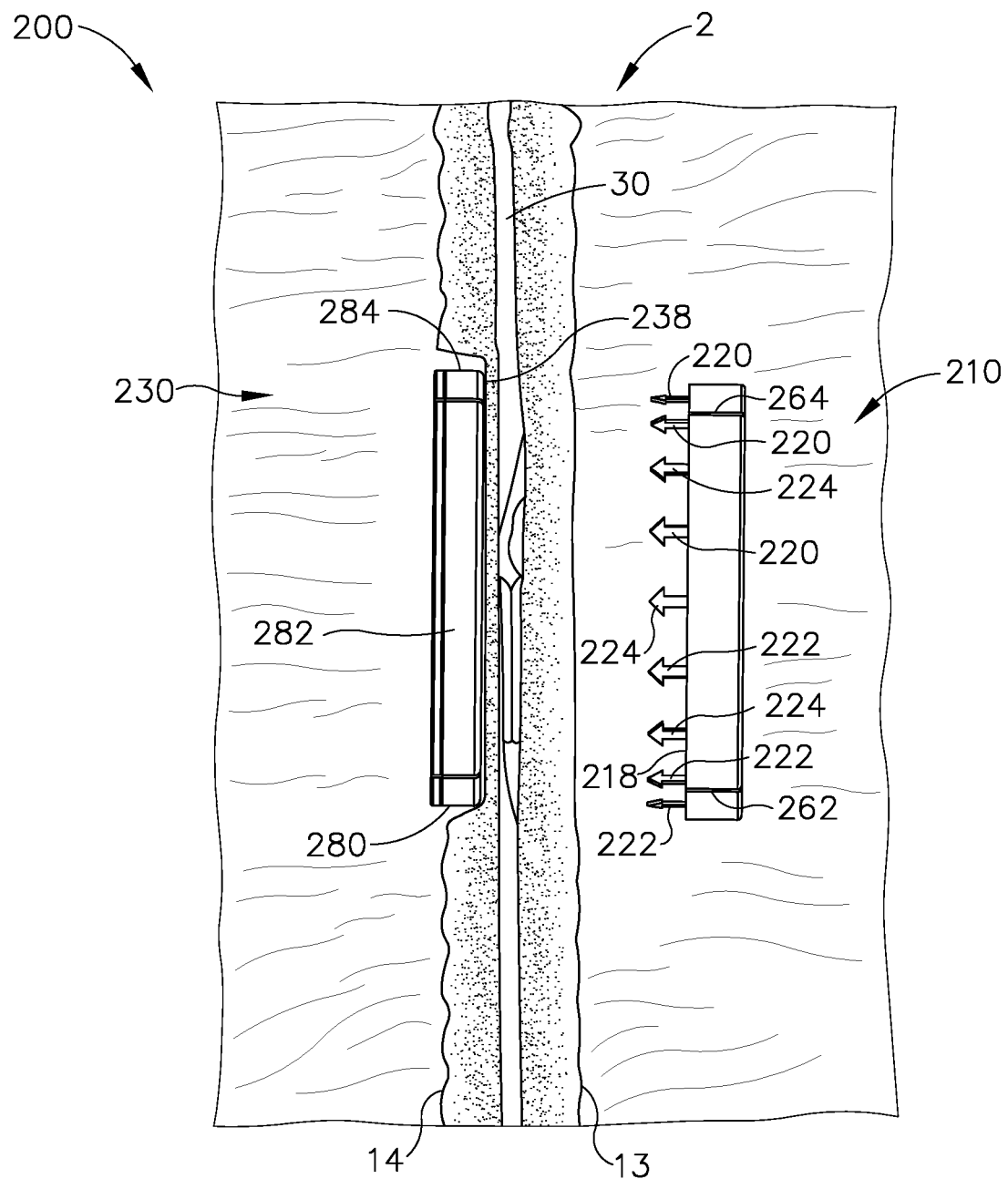
FIG. 14C depicts a cross-sectional view of the portions of the anastomosis compression device of FIG. 9 opposingly positioned in a patient's small intestine, with live tissue positioned between opposing surfaces of the anastomosis compression device portions.

As best seen in FIG. 14C, between inner surface (218) of first portion (210) and inner surface (238) of second portion (230) of the exemplary anastomotic compression ring (200) is a layer of tissue (30) from each of first lumen wall (13) and second lumen wall (14). Inward compression upon first portion (210) and second portion (230) of the anastomotic compression ring (200) correspondingly compresses against the captured tissue (30). Joining members (260, 262, 264) of first portion (210) and joining members (280, 282, 284) of second portion (230) maintain their structure and composition while remaining fully intact despite their initial exposure to the gastrointestinal tract of the patient's body.

Figure 14D:
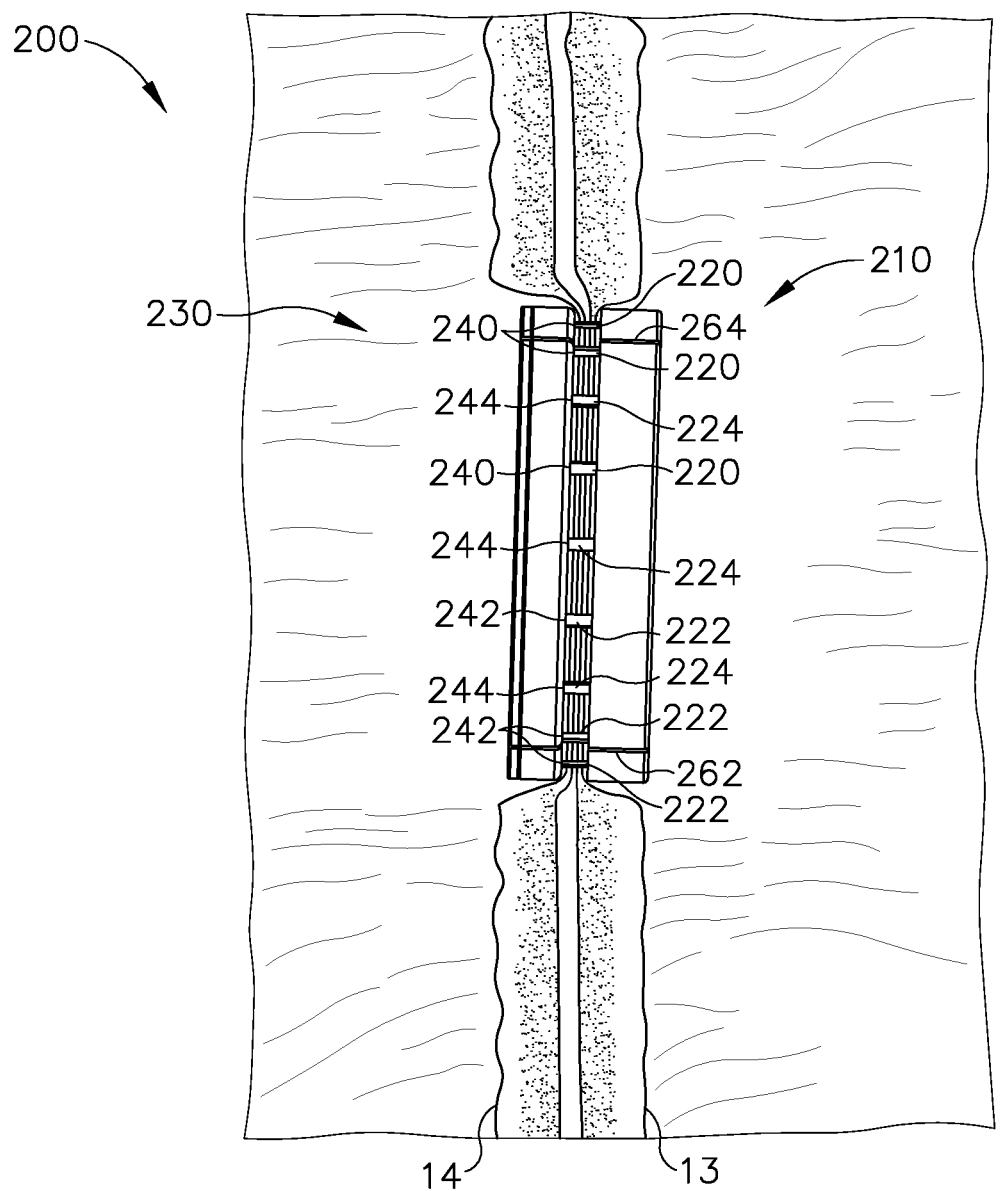
FIG. 14D depicts a cross-sectional view of the portions of the anastomosis compression device of FIG. 9 opposingly positioned in the patient's small intestine, with needles of the first portion of the anastomosis compression device piercing the tissue and being received within the second portion of the anastomosis compression device.

By compressing portions (210, 230) toward each other, interlocking mechanisms (220, 222, 224) of first portion (210) are urged toward corresponding interlocking mechanisms (220, 222, 224) of second portion (230). Interlocking mechanisms (240, 242, 244) of second portion (230) press against lumen wall (14) and interlocking mechanisms (220, 222, 224) of first portion (210) press against lumen wall (13) until the force applied exceeds the tensile strength of lumen wall (13). Subsequently, interlocking mechanisms (220, 222, 224) of first portion (210) pierce through lumen walls (13, 14) and as a result thereby allow interlocking mechanisms (220, 222, 224) of first portion (210) to engage and fasten with corresponding interlocking mechanisms (220, 222, 224) of second portion (230), as seen in FIG. 14D. This engagement secures first portion (210) relative to second portion (230).

Figure 13:
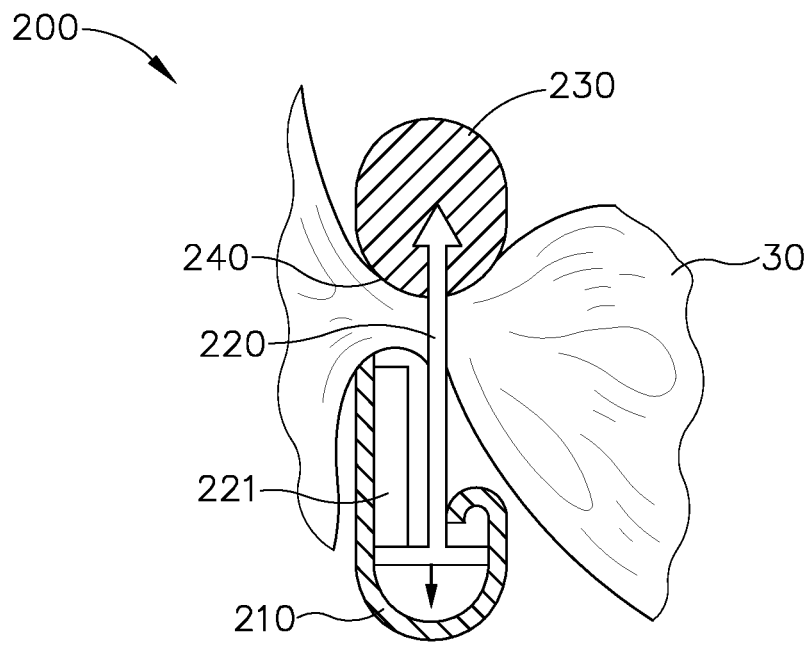
FIG. 13 depicts a cross-sectional view of the anastomosis compression device of FIG. 9 with tissue positioned between the opposing surfaces of the anastomosis compression device portion and pierced by a needle urged upwardly by the compression spring of the anastomosis compression device.

Over a period of time, the ischemia of tissue (30) caused by the compression of first portion (210) and second portion (230) of anastomotic compression ring (200) eventually results in necrosis of tissue (30). As shown in FIG. 13, interlocking mechanism (220) of first portion (210) includes a spring (221) that resiliently biases the needle of interlocking mechanism (220) toward the slot of interlocking mechanism (240) of second portion (230). As tissue (30) between first portion (210) and second portion (230) beings to necrose and thereby decrease in thickness, spring (221) propels interlocking mechanism (220) further into interlocking mechanism (240) of second portion (230). Although not shown, it should be apparent that interlocking mechanisms (222, 224) of first portion (210) also include springs (223, 225) that resiliently bias respective needles toward the slots of interlocking mechanisms (242, 244) of second portion (230).

Figure 14E:
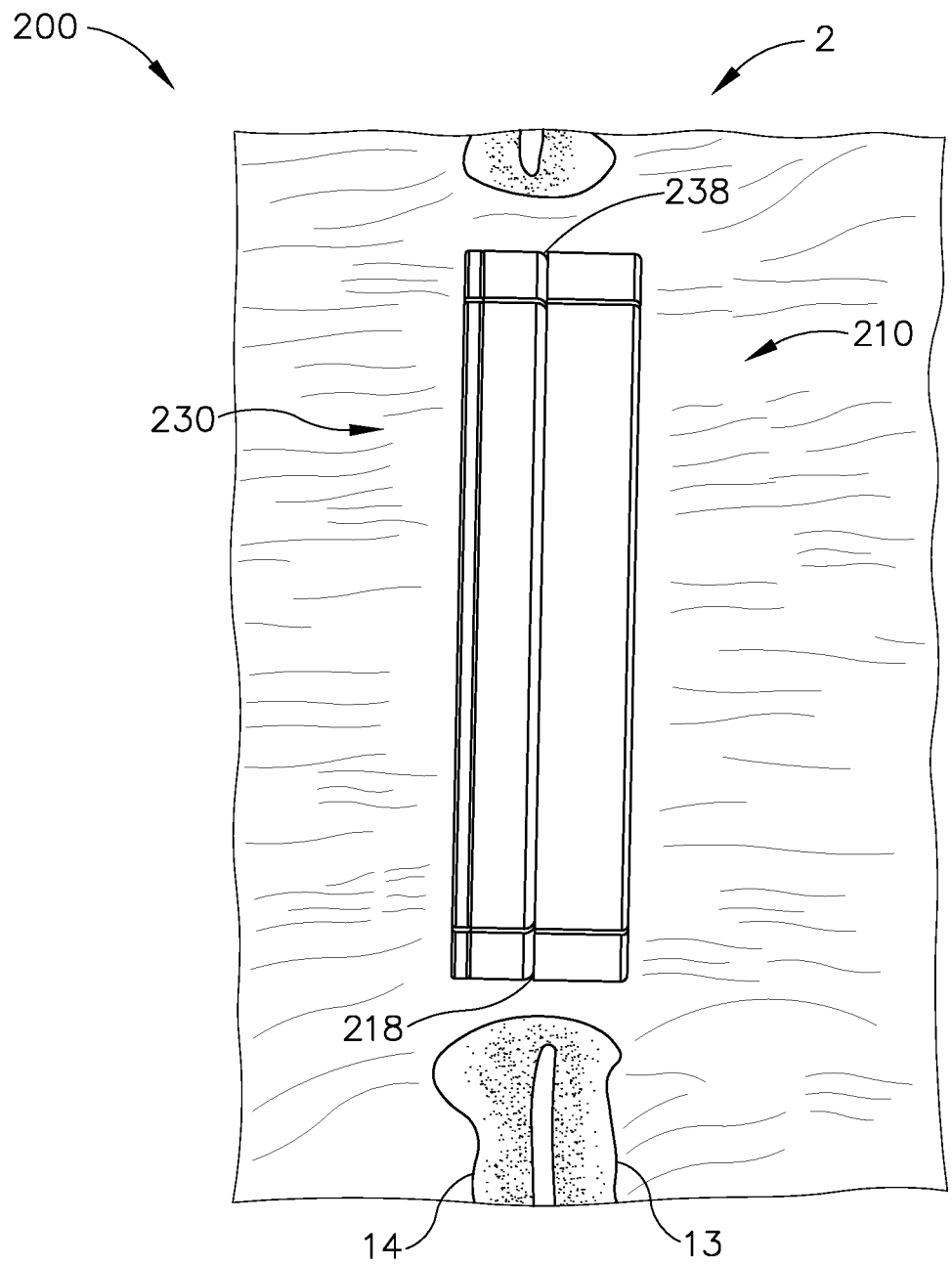
FIG. 14E depicts a cross-sectional view of the portions of the anastomosis compression device of FIG. 9, with the tissue positioned between the opposing surfaces of the anastomosis compression device portions in a state of necrosis, with the anastomosis compression device portions beginning to leave the anastomosis formed between the portions of the patient's small intestine.
Figure 14F:
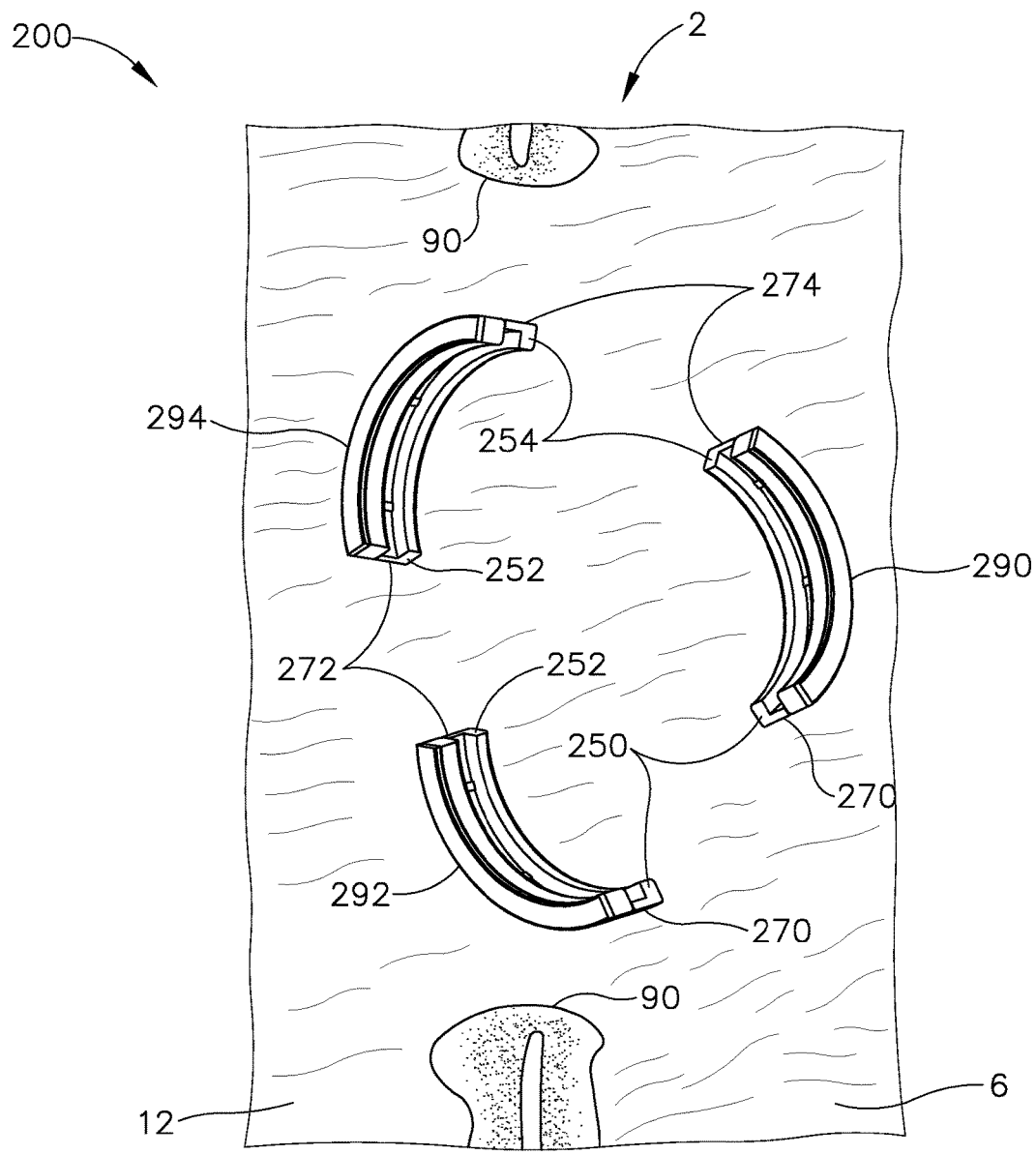
FIG. 14F depicts a cross-sectional view of the portions of the anastomosis compression device of FIG. 9, with the biodegradable joining members connecting the segments of the anastomosis compression device portions having degraded to cause the non-degradable segments of the anastomosis compression device portions to break apart, with the non-biodegradable segments passing through the remainder of the patient's digestive system while leaving behind a secure anastomosis.

As seen in FIG. 14E, the necrosis of tissue (30) eventually reaches a point where lumen walls (13, 14) can no longer structurally support anastomotic compression ring (200) such that anastomotic compression ring (200) breaks free from the site of the anastomosis (2). First portion (210) and second portion (230) of anastomotic compression ring (200) remain held together through the engagement of interlocking mechanisms (220, 222, 244) of first portion (210) and interlocking mechanisms (240, 242, 244) of second portion (230) so that inner surface (218) of first portion (210) and inner surface (238) of second portion (230) are securely pressed against each other. Since anastomotic compression ring (200) has now been exposed to the gastrointestinal tract of the patient's body for an amount of time in excess of the predetermined amount tolerable by joining members (260, 262, 264) of first portion (210) and joining members (280, 282, 284) of second portion (230), joining members (260, 262, 264, 280, 282, 284) have degraded and are no longer fixed at their original positions along edges (250, 252, 254) of first portion (210) and edges (270, 272, 274) of second portion (230). Due to this, anastomotic compression ring (200) no longer maintains structural support along edges (250, 252, 254, 270, 272, 274), thus causing anastomotic compression ring (200) to segment into a first fragment (290), second fragment (292) and a third fragment (294), as seen in FIG. 14F.

The segments (212, 232) of first portion (210) and second portion (230) comprising first fragment (290) remain held together due to the engagement of interlocking mechanisms (220, 240). Similarly, the segments (214, 234) of first portion (210) and second portion (230) comprising second fragment (292) remain held together due to the engagement of interlocking mechanisms (222, 242). Also similarly, the segments (216, 236) of first portion (210) and second portion (230) comprising third fragment (294) remain held together due to the engagement of interlocking mechanisms (224, 244). First fragment (290), second fragment (292) and third fragment (294) of anastomotic compression ring (200) will then pass into the ileum (6) and eventually pass into the bowels and out from the patient with feces. When anastomotic compression ring (200) leaves the site of the anastomosis (2), the structural integrity of the anastomosis (2) remains secure due to natural tissue adhesions. In particular, the exterior of the duodenum (12) and the ileum (6) may have substantial serosa-to-serosa adhesion at this point, due to the sustained contact between the duodenum (12) and the ileum (6). In addition, the mucosa at the interior of the duodenum (12) and the ileum (6) may have remodeled itself to provide a smooth mucosal transition (90) between the duodenum (12) and the ileum (6) at the site of the anastomosis (2), as shown in FIG. 14F. With the anastomosis (2) complete, chyme may freely pass from the duodenum (12) to the ileum (6) via the anastomosis (2), without needing to pass through the jejunum (4).

III. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An anastomosis compression assembly, comprising: (a) a first portion, comprising: (i) a first segment, (ii) a second segment, (iii) a first plurality of interlocking features, and (iv) a first biodegradable joining member securing the first and second segments together; and (b) a second portion, comprising: (i) a third segment, (ii) a fourth segment, (iii) a second plurality of interlocking features, wherein the second plurality of interlocking features are configured to engage the first plurality of interlocking features to thereby secure the first and second portions together, and (iv) a second biodegradable joining member securing the third and fourth segments together.

Example 2

The anastomosis compression assembly of Example 1, wherein the first portion has an inner surface shaped to complement an inner surface of the second portion.

Example 3

The anastomosis compression assembly of any one or more of Examples 1 through 2, wherein the first segment, the second segment, the third segment, and the fourth segment are each semi-circularly shaped.

Example 4

The anastomosis compression assembly of Example 3, wherein the first and second segments together define a circular shape with a central opening, wherein the third and fourth segments together define a circular shape with a central opening.

Example 5

The anastomosis compression assembly of any one or more of Examples 1 through 4, wherein the first plurality of interlocking features are located on a first surface of the first portion, wherein the first biodegradable joining member is located on a second surface of the first portion, wherein the second surface is opposite to the first surface.

Example 6

The anastomosis compression assembly of any one or more of Examples 1 through 5, wherein the first and second segments are formed of a non-biodegradable material.

Example 7

The anastomosis compression assembly of any one or more of Examples 1 through 6, wherein first and second portions are configured to form an annular shape when the first and second portions are coupled together.

Example 8

The anastomosis compression assembly of any one or more of Examples 1 through 7, wherein the first plurality of interlocking features includes latches, wherein the second plurality of interlocking features includes catches.

Example 9

The anastomosis compression assembly of Example 8, wherein the first plurality of interlocking features comprise needles.

Example 10

The anastomosis compression assembly of any one or more of Examples 1 through 9, wherein the first and second biodegradable joining members are formed of non-biodegradable material.

Example 11

The anastomosis compression assembly of any one or more of Examples 1 through 10, wherein the first segment provides a first surface area, wherein the first biodegradable joining member provides a second surface area, wherein the first surface area is larger than the second surface area.

Example 12

The anastomosis compression assembly of any one or more of Examples 1 through 11, wherein the first biodegradable joining member is secured to the first and second segments by pins.

Example 13

The anastomosis compression assembly of any one or more of Examples 1 through 12, wherein the first segment provides a first cross-sectional area, wherein the first biodegradable joining member provides a second cross-sectional area, wherein the first cross-sectional area is larger than the second cross-sectional area.

Example 14

The anastomosis compression assembly of any one or more of Examples 1 through 13, wherein the first plurality of interlocking features includes a needle and a spring, wherein the spring is configured to bias the needle toward the second portion.

Example 15

The anastomosis compression assembly of Example 14, wherein the second plurality of interlocking features includes an opening configured to receive the needle.

Example 16

An anastomosis compression assembly, comprising: (a) a first half, comprising: (i) a first segment comprising: (1) a first surface, (2) a second surface, and (3) a first engagement feature protruding from the first surface of the first segment, and (ii) a second segment comprising: (1) a first surface, (2) a second surface, and (3) a second engagement feature protruding from the first surface of the second segment, (iii) a biodegradable connector connecting the first segment with the second segment; and (b) a second half, comprising: (i) a third segment comprising: (1) a first surface, (2) a second surface, and (3) a third engagement feature, wherein the third engagement feature is configured to engage the first engagement feature to thereby couple the first segment with the third segment, and (ii) a fourth segment comprising: (1) a first surface, (2) a second surface, and (3) a fourth engagement feature, wherein the fourth engagement feature is configured to engage the second engagement feature to thereby couple the second segment with the fourth segment, (iii) a biodegradable connector connecting the third segment with the fourth segment.

Example 17

The anastomosis compression assembly of Example 16, wherein the first and second segments are coplanar with each other.

Example 18

The anastomosis compression assembly of any one or more of Examples 16 through 17, wherein the first and second segments adjoin each other along adjacent edges.

Example 19

The anastomosis compression assembly of any one or more of Examples 16 through 18, wherein the biodegradable connector spans across at least a portion of the second surface of the first segment and across at least a portion of the second surface of the second segment.

Example 20

A method of forming an anastomosis in a patient's gastrointestinal tract, wherein the method comprises: (a) positioning a first tissue compression member in a first region the gastrointestinal tract, wherein the first tissue compression member comprises two or more segments joined together by one or more biodegradable joining members; (b) positioning a second tissue compression member in a second region the gastrointestinal tract, wherein the second tissue compression member comprises two or more segments joined together by one or more biodegradable joining members; (c) compressing tissue between the first and second tissue compression members in the first and second regions of the gastrointestinal tract, and (d) securing the first and second tissue compression members to maintain compression of the tissue, wherein the biodegradable joining members are configured to degrade while the first and second tissue compression members are in the gastrointestinal tract, to thereby result in the first and second tissue compression members breaking up into the segments.

IV. MISCELLANEOUS

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:
1. An anastomosis compression assembly, comprising:
    (a) a first portion, comprising:
        (i) a plurality of first portion segments,
        (ii) a plurality of first portion interlocking features, wherein each of the first portion segments includes a respective one or more of the first portion interlocking features, and
        (iii) a plurality of first portion biodegradable joining members, wherein each of the first portion biodegradable joining members is directly secured to and thereby couples together a respective pair of the first portion segments; and
    (b) a second portion, comprising:
        (i) a plurality of second portion segments,
        (ii) a plurality of second portion interlocking features, wherein each of the second portion segments includes a respective one or more of the second portion interlocking features, wherein the second portion interlocking features are configured to engage the first portion interlocking features to thereby secure each of the first portion segments to a respective one of the second portion segments, and
        (iii) a plurality of second portion biodegradable joining members, wherein each of the second portion biodegradable members is directly secured to and thereby couples together a respective pair of the second portion segments.

2. The anastomosis compression assembly of claim 1, wherein the first portion has an inner surface shaped to complement an inner surface of the second portion.

3. The anastomosis compression assembly of claim 1, wherein each of the first portion segments and the second portion segments is semi-circularly shaped.

4. The anastomosis compression assembly of claim 3, wherein the first portion segments together define a circular shape with a central opening, wherein the second portion segments together define a circular shape with a central opening.

5. The anastomosis compression assembly of claim 1, wherein the first portion interlocking features are located on a first side of the first portion, wherein the first portion biodegradable joining members are located on a second side of the first portion, wherein the second side is opposite to the first side.

6. The anastomosis compression assembly of claim 1, wherein the first portion segments are formed of a non-biodegradable material.

7. The anastomosis compression assembly of claim 1, wherein the first and second portions are configured to form an annular shape when the first and second portions are coupled together.

8. The anastomosis compression assembly of claim 1, wherein the first portion interlocking features include latches, wherein the second portion interlocking features include catches.

9. The anastomosis compression assembly of claim 8, wherein the first portion interlocking features comprise needles.

10. The anastomosis compression assembly of claim 1, wherein at least one of the first portion interlocking features or the second portion interlocking features are formed of non-biodegradable material.

11. The anastomosis compression assembly of claim 1, wherein a first segment of the first portion segments provides a first surface area, wherein a first biodegradable joining member of the first portion biodegradable joining members provides a second surface area, wherein the first surface area is larger than the second surface area.

12. The anastomosis compression assembly of claim 1, wherein the first portion biodegradable joining members are secured to the first portion segments by pins.

13. The anastomosis compression assembly of claim 1, wherein a first segment of the first portion segments provides a first cross-sectional area, wherein a first biodegradable joining member of the first portion biodegradable joining members provides a second cross-sectional area, wherein the first cross-sectional area is larger than the second cross-sectional area.

14. The anastomosis compression assembly of claim 1, wherein the first portion interlocking features include a needle and a spring, wherein the spring is configured to bias the needle toward the second portion.

15. The anastomosis compression assembly of claim 14, wherein the second portion interlocking features include an opening configured to receive the needle.

16. An anastomosis compression assembly, comprising:
    (a) a first half, comprising:
        (i) a non-biodegradable first segment comprising:
            (1) a first surface,
            (2) a second surface, and
            (3) a first engagement feature protruding from the first surface of the first segment, (ii) a non-biodegradable second segment comprising:
   (1) a first surface,
   (2) a second surface, and
   (3) a second engagement feature protruding from the first surface of the second segment,
   wherein an end of the second segment confronts an end of the first segment, and
(iii) a biodegradable connector connecting the confronting ends of the first segment and the second segment; and
(b) a second half, comprising:
   (i) a non-biodegradable third segment comprising:
      (1) a first surface,
      (2) a second surface, and
      (3) a third engagement feature, wherein the third engagement feature is configured to engage the first engagement feature to thereby couple the first segment with the third segment,
   (ii) a non-biodegradable fourth segment comprising:
      (1) a first surface,
      (2) a second surface, and
      (3) a fourth engagement feature, wherein the fourth engagement feature is configured to engage the second engagement feature to thereby couple the second segment with the fourth segment,
      wherein an end of the third segment confronts an end of the fourth segment, and
   (iii) a biodegradable connector connecting the confronting ends of the third segment and the fourth segment.

17. The anastomosis compression assembly of claim 16, wherein the first and second segments are coplanar with each other.

18. The anastomosis compression assembly of claim 16, wherein the first and second segments adjoin each other along adjacent edges.

19. The anastomosis compression assembly of claim 16, wherein the biodegradable connector overlies at least a portion of the second surface of the first segment and overlies at least a portion of the second surface of the second segment.

20. A method of forming an anastomosis in a patient's gastrointestinal tract, wherein the method comprises:
(a) positioning a first tissue compression member in a first region of the gastrointestinal tract, wherein the first tissue compression member comprises two or more first member segments joined together by one or more biodegradable joining members, wherein each of the first member segments includes a first coupling feature;
(b) positioning a second tissue compression member in a second region of the gastrointestinal tract, wherein the second tissue compression member comprises two or more second member segments joined together by one or more biodegradable joining members, wherein each of the second member segments includes a second coupling feature;
(c) engaging each of the first coupling features with a respective second coupling feature to thereby couple each of the first member segments with a respective second member segment;
(d) compressing tissue between the first and second tissue compression members in the first and second regions of the gastrointestinal tract; and
(e) securing the first and second tissue compression members together to define a compression assembly that maintains compression of the tissue, wherein the compression assembly is defined in its entirety by a plurality of compression assembly sections, wherein each of the compression assembly sections comprises one of the first member segments and one of the second member segments secured together by the respective first and second coupling features;
wherein the biodegradable joining members are configured to degrade while the compression assembly is in the gastrointestinal tract such that the compression assembly separates into the plurality of compression assembly sections.

\* \* \* \* \*